United States Patent [19]

Brodsky et al.

[11] Patent Number: 4,971,954

[45] Date of Patent: Nov. 20, 1990

[54] COLLAGEN-BASED MATRICES RIBOSE CROSS-LINKED

[75] Inventors: Barbara Brodsky, Princeton Junction; Richard A. Berg, Lambertville; Gad Avigad, New York; Eric Eikenberry, Princeton; Manoj Jain, Piscataway, all of N.J.; Shizuko Tanaka, Odawane, Japan

[73] Assignee: University of Medicine and Dentistry of New Jersey, Newark, N.J.

[21] Appl. No.: 275,807

[22] Filed: Nov. 23, 1988

[51] Int. Cl.$^5$ .................. C07K 15/20; C08L 89/06
[52] U.S. Cl. .................................. 514/21; 530/356; 604/368
[58] Field of Search .................. 530/356; 604/368; 514/21

[56] References Cited

PUBLICATIONS

Lien et al., Science, 225, pp. 1489–1491 (Sep. 1984).
Fujimoto et al., Experientia 42(1986), 4 p. 405.
Kent et al., Biochem. J. 225(3), 745–752 (1985).

*Primary Examiner*—Lester L. Lee
*Assistant Examiner*—C. Koh
*Attorney, Agent, or Firm*—Weiser & Stapler

[57] ABSTRACT

Stabilized collagen-based matrices are prepared by non-enzymatic glycosylation of native collagen to irreversibly cross-link collagen polypeptide chains. The sugar cross-linking agents, preferably is D-ribose, provide non-immunogenic, non-toxic cross-linked collagen matrices especially useful in clinical and veterinary applications.

21 Claims, 10 Drawing Sheets

CROSS-LINKS DECREASE DIGESTION BY VERTEBRATE COLLAGENASE

COLLAGEN-BASED MATRICES RIBOSE CROSS-LINKED

BACKGROUND OF THE INVENTION

Collagen is a potentially useful biomaterial owing to its formation as a natural polymer, its ready availability, its biocompatibility and its inherent strength. As a result, collagen-based matrices are widely used, especially in clinical applications requiring the use of a relatively stable, biodegradable polymer. Such matrices are particularly employed as implants in a variety of surgical and medical procedures. They are generally prepared for this use by purifying native collagen and cross-linking the purified fibers to increase the mechanical strength of the matrix and improve resistance to enzymatic degradation.

When collagen is obtained from animals, usually in the form of hides or bones, various contaminating tissue macromolecules and blood must be removed and the collagen purified in order to be reused. Collagen normally has to be ground, shredded or pulverized, washed extensively with various solvents and reformed into various materials. Collagen particles and fibers so produced must be recross-linked in order to regain the strength and physical properties which allow it to be used as a biomaterial. Agents used for cross-linking collagen have been described for centuries in terms of its being tanned for use as leather. Various methods of cross-linking collagen have been used for this purpose; however, most methods used for cross-linking collagen, including some methods that allow collagen to be cross-linking as bioimplantable devices, have proven to be toxic for cell growth, and/or not biocompatible as implants.

Until recently, the cross-linking agents of choice have been glutaraldehyde and related non-physiological agents, which react with amino acid residues in the collagen molecule to cross-link polypeptide chains. The use of such cross-linking agents to prepare collagen matrices for clinical or veterinary applications is currently in disfavor, however, owing to the incidence of toxic and immunogenic reactions attributed to leaching of these agents from the matrix into the surrounding body areas of the host. Localized inflammation and more complex systemic reactions are particularly common side-effects of collagen-based implants cross-linked with glutaraldehyde. Further, such cross-linking agents tend to unfavorably alter the collagen amino acids side chains that reduces cell attachment resulting in a matrix that does not promote cell ingrowth from the host. Such cross-linked materials are susceptible to being either walled off or, promoting foreign body reactions.

Accordingly, other, more physiologically-acceptable, cross-linking agents have been proposed for stabilizing collagen matrices, such as the carbodiimide or succinimidyl active ester agents described in U.S. Pat. No. 4,703,108. The cross-linking process described in this patent, however, requires a relatively harsh dehydrathermal step, and precludes the incorporation of heat-sensitive components into the collagen matrix in conjunction with the cross-linking reaction.

SUMMARY OF THE INVENTION

The invention provides a glycated collagen-based matrix especially useful as an implant in clinical and veterinary applications prepared by non-enzymatic glycosylation of native collagen fibrils to irreversibly cross-link collagen polypeptide chains. The sugar of choice is D-ribose. The sugars employed as cross-linking agents especially D-ribose are typically non-toxic and non-immunogenic, and the cross-linked residues are characterized by an intrinsic fluorescence readily detected in standard fluorescence assays. Since the degree of cross-linking correlates well with mechanical and biodegradation characteristics of the matrix, the matrix can be readily biostabilized as desired by monitoring the increase in fluorescence during cross-linking. Further, since the process conditions for glycosylation according the invention are mild, heat-sensitive components can be incorporated into the matrix during cross-linking, and in situ cross-linking of implants is practicable.

The present invention relates to the use of certain carbohydrates to cross-link collagen to form non-toxic biocompatible materials without resorting to severe dehydration at high temperatures or the addition of even catalytic amounts of organic chemicals, permits the production of cross-linked collagen in a number of different forms which are suitable for bioimplantation and which support the growth of connective tissue cells. When collagen is formulated into a sponge having a geometry which allows fibroblast ingrowth, and cross-linked with carbohydrate, the final collagen sponge is both biocompatible, non-toxic and supports the growth of connective tissue cells. Such material is suitable for use as biological implants in the form for example, of sheets, tubes, beads, and also for use as a collagen sponge for hemostasis and wound dressings.

DETAILED DESCRIPTION OF THE INVENTION

Figure 1:
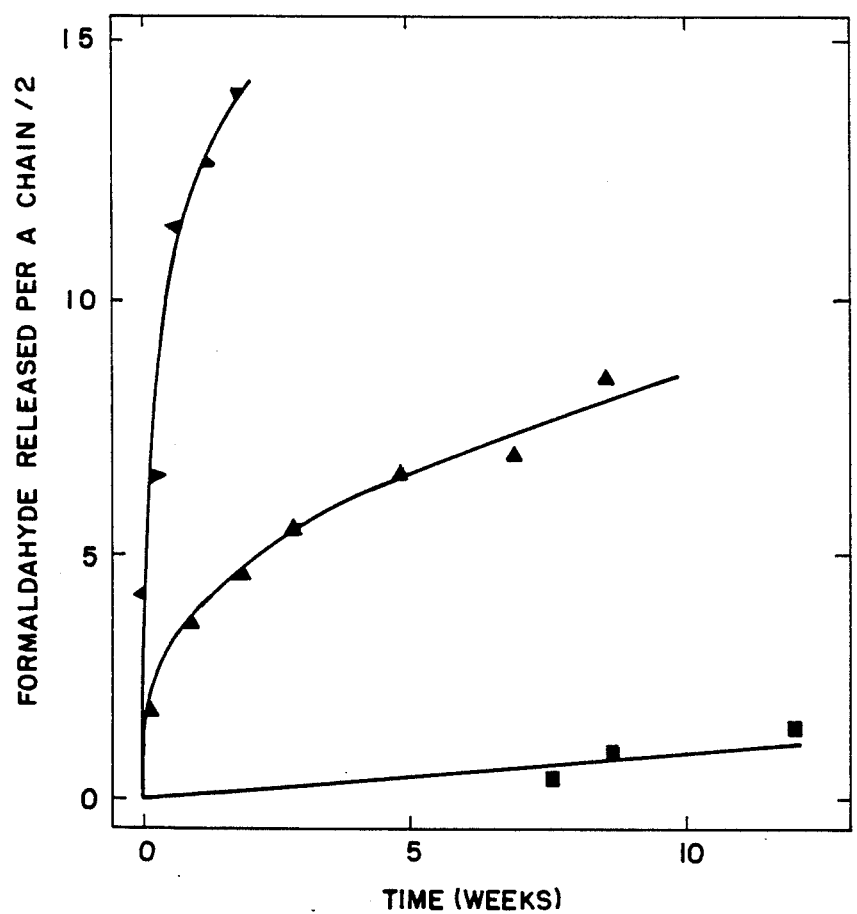
FIG. 1. —Glycation of rat tail tendon collagen by various sugars. The ordinate is expressed as moles of formaldehyde formed per mole of $\alpha$ chain in the absence of cross-links.
Symbols: (▲), 0.20 M D-glucose; (■), 0.20 M D-ribose; (●), 0.025 M DL-glyceraldehyde.

Glycation (i.e., non-enzymatic glycosylation) of collagen has been described in the literature by the inventors herein and others, particularly in studies examining the role of glucose in vivo in the gradual deterioration of connective tissue during the aging process, and in connective tissue changes associated with hyperglycemia. These studies have characterized in vivo glycation of collagen as the covalent attachment of the carbonyl group of glucose to free amino groups of the collagen molecule, followed by condensation of two or more of the altered amino groups to form highly stable linkages between collagen polypeptide chains, and have attributed the mentioned connective tissue changes to in vivo cross-linking of collagen with glucose over time.

The present invention is predicated on the discovery that non-toxic, non-antigenic collagen-based matrices for commercial use having good mechanical and biochemical stability are obtained by glycation of native collagen fibers with a reducing sugar or derivative thereof, especially D-ribose, under controlled reaction parameters including sugar concentration, incubation time and temperature, and selection of sugar cross-linking agent. The reaction is monitored by standard fluorescence assay to assess the degree of cross-linking, which has been found to correlate with the degree of mechanical stability of the matrix and its resistance to enzymatic degradation. These properties are thus accurately modulated to suit the desired application, by contemporaneous adjustment of reaction conditions.

The reducing sugar that may be employed to cross-link the collagen molecules according to the invention is a reducing sugar, especially monosaccharides more particularly D-ribose, having a high relative reactivity with α- or ε- amino functional groups on the collagen molecule, to form a ketoamine or aldimine adduct via the following mechanism (I)

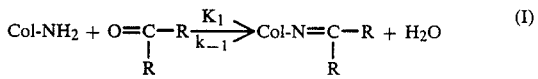

(I)

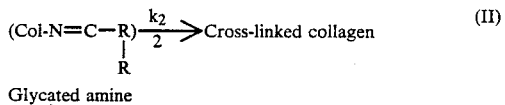

(II)

Glycated amine wherein

is the free open-chain aldehyde or keto form of the reducing sugar and Col is collagen. The Schiff base product (imine) non-enzymatically rearranges to a more stable ketoamine linkage by Amadori rearrangement. This process, referred to herein as glycation or non-enzymatic glycolysis, is followed, under appropriate reaction conditions, by spontaneous condensation of two or more ketoamine groups or two or more ketoamine and amino group in proximity to form incompletely characterized intra- or intermolecular linkages which irreversibly cross-link different domains of the collagen molecule or two or more collagen molecules. In fibrillar collagen, wherein the α-amino groups are blocked against reaction with the sugar carbonyls, the ε-amino groups participating in the reaction appear to be at least primarily associated with lysyl and hydroxylysyl residues in the collagen molecule. The cross-linkages are intrinsically highly fluorescent, and readily quantified by standard fluorometric assay procedures.

The above description refers to a sugar preferred at this time. The invention, however, contemplates also other carbohydrates of the formula $-(CH_2O)_n-$ wherein n can be an integer from 3 to preferably not over 6. Thus, there are contemplated pentoses like d-arabinose, d-lyxose, d-xylose, l-rhamose, (and of course d-ribose already discussed above); the hexoses like d-glucose, d-manose, d-galactose, d-idose, d-gulose; ketoses like d-fructose, or d-sorbose. An additional reason for preferring ribose is that it has a higher acyclic aldehyde concentration (0.05%) than the other pentoses. Amongst the sugars, the naturally occcuring sugars are generally preferred.

Especially where the ultimate application of the collagen product is intended for contact with or into human (or mammals) body parts, such sugars are expected to be more compatible, less likely to elicit rejection by the human immune system, more bioacceptable (and when so desired, biodegradable) than previously used cross-linking agents.

Cross-linking of collagen with reducing sugars as a group proceeds relatively slowly as compared to glutaraldehyde, for example, although sugars within the groups discussed above vary considerably in their reactivity with collagen. To obtain collagen-based matrices for use according to the invention within a commercially practical processing time, the reducing sugar employed ideally should have a sufficiently high reactivity with collagen preferably no more than about one week or even a matter of a few hours (such as 1 to 6 hrs.).

For use according to the invention, especially clinical use, sugars which react with the collagen starting material to provide a matrix stiffness modulus of at least about 2 mPa, preferably at least about 4 mPa, (as measured, for example, by the procedure set forth in Example II) within no more than about 2 weeks, preferably no more than about 1 week, herein referred to as "reactive reducing sugars" are generally suitable cross-linking agents within the scope of the invention.

Sugars such as glucose, which may require up to about several weeks to cross-link to a desired mechanical strength, are generally not recommended. A combination of two or more reducing sugars may be employed, or the reducing sugar may be employing in conjunction with other collagen cross-linking agents or methods.

A forward reaction rate for glycation ($k_1$, Equation I) of at least about $9.0 \times 10^{-3}$/mM/hour and/or a reaction rate for cross-linking ($k_2$, Equation II) of at least about from an hour to several days will generally provide a matrix having significantly improved mechanical properties within an acceptable time period.

It should be noted that the rate of reaction of the sugar with the collagen can be influenced by various factors including varying the temperature at which the reaction is carried. Normally higher temperatures will increase the rate of cross-linking so that the upper limit of the temperature will generate the temperature at which collagen fibrils (for instance, tendon, sponges, or the like) are thermally stable.

An upper limit that may be considered may be approaching the 50°-60° C. range. Thus, the process of the invention contemplates a range from about room temperature, e.g. about 20° C. to about 50° C. Likewise the speed of the reaction can be promoted by varying (e.g., increasing) the pressure from atmospheric to above atmospheric.

It should also be noted that the concentration of the sugar may be increased to where the viscosity of the reaction mixture would exceed a workable viscosity. However, with appropriate variations of temperatures (and/or pressures), the viscosity may be reduced and possibly higher (or super-saturated) sugar concentrations used in the process for making the products of the invention.

For industrial production, it can be visualized that collagen fibers, (fibrils, mats, slabs, etc.) can be passed through appropriate containers on a continuous (or batch-wise) basis, the containers containing the cross-linking sugar (or mixtures thereof) and being under the selected conditions of temperature, pressure, (exposed to air or other gases) as may be considered appropriate. The liquid reacting mixture may also contain any chemical which does not adversely affect the reaction such a surface active agent, chemical for lowering the surface tension, catalysts, etc.

As will become even more apparent, it is the cross-linking of the collagen fibrils (or fibers) with an appropriate sugar like d-ribose which is an important part of the invention, and less the specifics how to achieve that end, for which this description is disclosing preferred conditions.

Reactive reducing sugars according to the invention generally comprise those sugars which have an equilibrium in the reaction solution which is more favorable (as compared to glucose) to the reactive acyclic form than to the non-reactive ring form of the molecule; for example, those monosaccharides wherein the reaction solution contains at least about 0.01% relative concentration of the acyclic aldehyde or keto (open chain) reactant per mol of monosaccharide, preferably at least about 0.05%, generally provide an adequate reaction rate. Since aldehyde forms are generally more reactive than keto forms at comparable concentrations, aldoses are generally employed over ketoses, all other things being equal. However, since reactivity of the monosaccharide is also dependent on other factors, such as the presence of a charge on the sugar molecule, as obtained for example, by forming an acid salt of the sugar, it is generally advisable to maximize reaction rates by selection of the sugar on the basis of overall reactivity with the polypeptide collagen chains. The other comments made above as to reactivity apply here also.

As noted above in Equation I, the glycation reaction $k_1$ is reversible, it may be desirable to optimize the reaction by blocking the reverse reaction $k_{-1}$, as by including a reducing compound which does not react with either the free monosaccharides or the reactive collagen amino groups in the reaction mixture. Such compound may be included in the reaction vessel, as described above.

According to the process of the invention, the collagen starting material is incubated with an aqueous solution of one or more of the selected reactive cross-linking sugars for a period of time sufficient to cross-link and insolubilize the collagen and to obtain the desired matrix stability. Biological temperatures (i.e., temperatures at which biological reactions are typically conducted) are employed for incubation, generally from between about 20° to about 60° C. The temperature should be sufficiently high to promote the reaction, and low enough to avoid substantial denaturation of the collagen starting material or product. The effect of high temperatures and other reaction conditions have been discussed above.

Concentrations of the selected sugar and/or time of reaction are carefully selected to avoid excess cross-linking and/or destabilization of the matrix. Fiber x-ray diffraction analysis indicates that, as cross-linking progresses, the orientation of the collagen molecules in the fiber is perturbed and the molecules are progressively pushed apart. It has been found in accordance with the invention that, beyond a critical point of cross-link concentration, the fibers, which have acquired an increasing mechanical stability via the cross-linking process, begin to destabilize, with deterioration of the mechanical strength of the matrix (FIG. 7). The destabilization has been associated with disruption of molecular organization, and, accordingly cross-linking should serve to separate the collagen molecules or chains without substantially disrupting molecular organization.

Based on x-ray crystallography studies, it appears that the amount and type of displacement of collagen molecules from their original orientation in the fiber caused by cross-linking of the collagen molecules by a given concentration of sugar varies according to the type of collagen employed. For example, in bovine Type I collagen, there are two sites in the molecule overlap zones where lysine residues are at the same axial position and potentially directly opposing; a cross-linkage at these sites would serve to push the overlapping molecules apart, while cross-linkages at other sites are potentially easily accommodated in the intermolecular interstices without perturbation of the structure. It is thus likely that only a subset of the cross-linked sugar residues cause the perturbation of the structure associated with destabilization of the matrix. The degree of cross-linking optimal for mechanical strength for a particular biomedical purpose will thus vary with collagen type, the process parameters of sugar type, sugar concentration, and time of reaction are selected to optimize the mechanical and biochemical properties of the product matrix. The binding of sugar molecules precedes cross-linking, and cross-linking of the collagen molecules via the bound sugar residues is site-dependent, thus the reaction kinetics are complex. While it has been observed that the production of cross-links is approximately linear with time for a given concentration of a selected cross-linking sugar, the production of cross-links (rate of cross-link formation) is not linearly dependent upon concentration of a given sugar (see, e.g., FIG. 1). Further, at a concentration above a certain point (herein referred to as "critical maximum concentration") reactive reducing sugars according to the invention exhibit anomalous behavior, which may result in the abrupt loss of matrix modulus, as illustrated in FIG. 7 for D-ribose, before the desired mechanical strength has been attained. This result is presumably due to destabilization of the matrix by excessive cross-link formation as described above, and sugar concentrations should be selected to avoid exceeding critical maximum concentrations for contemplated reaction parameters. Since increase in mechanical stability of the matrix (e.g., increase in modulus) directly and closely correlates with increase in cross-linkages, a useful starting point for selecting reaction parameters for a given sugar type is to correlate the desired matrix properties with the degree of cross-linking (cross-linkage concentration) required to obtain these properties. This is conveniently accomplished by fluorometric assay for the highly fluorescent cross-linked sugar residues. The Examples below illustrate this aspect. The theoretical amount of sugar required for cross-linking a given collagen starting material to the desired degree may be determined by calculating the desired cross-linkage content against the collagen α-chain content, as the reducing sugars of the invention substantially exclusively cross-link collagen α-chains. A standard assay for collagen α-chain content, such as the Berg hydroxyproline assay described in the Examples, is suitably employed for this purpose. In general, the mol ratio of cross-linked sugar residues to α-chain collagen content should not exceed about 1:1 to avoid destabilization of the matrix, and at least a sufficient number of cross-linkages should be present to substantially improve stability of the matrix, for example, a mol ratio of cross-linked sugar residues to α-chain collagen of at least about 0.1:1 to higher ratios. Once the optimum cross-linkage content for a given collagen type of desired properties is established, the concentration of sugar in the incubation solution and/or the time of reaction and other reaction conditions are adjusted to provide this result, without exceeding a critical maximum sugar concentration. In general, a concentration of reactive reducing sugar in the reaction solution of from about 2 to 50mM and reaction times, of from about 1 to 2 weeks are contemplated for producing matrices within the scope of the invention, depending on the reactivity of the sugar or sugars employed, and the molecular organization and biochemical characteristics of the starting collagen material. Incubation solution concentration solution concentrations of D-ribose of from about 0.1 M to 0.2 M are particularly suitable, but higher proportions may be used, as discussed above.

The collagen starting material is not critical to the invention. In general any known native collagen type (e.g., types I–V) may be employed, particularly type I collagen. Cross-linking of the triple helical domains of different collagen molecules renders the collagen highly insoluble to CNBr or pepsin digestion. Typically, either native insoluble collagen is recovered from, for example, collagenous tissues of a mammal such as bovine hide, or native soluble collagen is extracted from a suitable biological source; the thus obtained crude collagen is usually purified and any dried in any appropriate way such as freeze-dried for storage. Freeze-dried collagen is reconstituted, often by swelling in acid solution. and formed into the desired form for the intended use, usually before cross-linking is carried out. A variety of methods are well-known in the art for preparing porous and non-porous collagen-based matrices suitable for cross-linking into sponges, flakes, gels, tubes, beads, flakes, sheets, and related physical and geometric forms, and all such pre-treated collagen is contemplated as collagen starting material according to the present invention, including collagen chemically or physicochemically modified with foreign components such as pharmaceuticals or synthetic polymers. Commercial collagen preparations such as Avitene (FMC Corp. Phila. Pa.) or similar products that are fibrillar collagen preparations, are also useful as collagen starting materials. Exemplary processes for the preparation of various types of native collagen for cross-linking according to the invention are set forth in U.S. Pat. No. 4,703,108, incorporated herein by reference. Other exemplary processes are disclosed in U.S. Pat. Nos. 4,412,947; 4,060,081; 4,418,691; 4,374,121; and 4,409,332. The matrices cross-linked according to the invention may also be post-treated as known in the art, as by layering the matrix with a synthetic polymer such as silicone.

To obtain the cross-linked collagen matrices according to the present invention, the selected reactive sugar is incubated with the starting material in a physiologically-acceptable reaction solution preferably at a pH of about neutral for the determined length of time; physiological saline or other solution which does not tend to denature the reactants is suitable. As previously noted, the process is particularly adapted to the preparation of cross-linked collagen-based matrices for clinical and veterinary use, especially implants, and the process parameters are adjusted to provide properties of mechanical strength and resistance to enzymatic or other biodegradation consistent with the contemplated use of the product.

Particular clinical applications include artificial skin, nerve regeneration tubes, artificial blood vessels, bone substitutes, hemostatic dressings, organ replacements, wound dressings, and drug delivery systems. The preparation of collagen-based matrices which may be stabilized by cross-linking into materials adapted for these uses is well-known in the art as described above, and the improvement herein lies in the use of the described reactive sugar cross-linking agents according to the disclosed process parameters to obtain the stabilized matrices. A particularly interesting application of cross-linked collagen-based matrices according to the invention is a dressing for skin wounds or burns, as the sugar-linked matrix promotes improved fibroblast attachment to the matrix and healing of the wound, in contrast to matrices cross-linked according to prior art processes (Example II).

Since it has been assumed that charges on the collagen molecule improve the ability of collagen to interact with cells (see e.g., U.S. Pat. No. 4,559,304), and since treatment of collagen with a carbohydrate according to the invention reduces the number of positively charged residues on the molecule, the capability of the products of the invention to promote fibroblast attachment, is quite unexpected.

For the preparation of products for clinical use, components which enhance the utility of the product in the contemplated application may be introduced into the product during or after processing, such as the proteins, growth factors, pharmaceuticals or enzymes described in U.S. Pat. No. 4,703,108. Since the present process employs mild conditions for cross-linking, in contrast, for example to the relatively harsh dehydrathermal step of this patent, even heat-sensitive materials may be incorporated during the cross-linking step, for example by conjugating the desired component to the cross-linking reactive reducing sugar according to known chemical principles. Cross-linked matrices for clinical use preferably are prepared from biological sugars which meet the criteria set forth to minimize toxicity and antigenicity; alternatively, non-biological sugars with low toxic or antigenic potential are preferably utilized in such application.

BEST MODE OF PRACTICE

Optimum conditions have been established for cross-linking collagen biomaterials using reducing sugars such as ribose. The collagenous tissue or material is incubated in a solution of 0.2 M ribose for a period of up to 48 hrs followed by washing to remove uncrosslinked ribose. The material can then be dehydrated by lyophilization drying or left in a hydrated state.

In accordance with this invention, optimum conditions have been established for manufacturing a collagen product, e.g. a sponge, which to date is most satisfactory. The process comprises dispersing a finely divided inorganic acid like hydrochloric acid at a pH preferably between about 1.0 and 4.0, even more preferably from about 2.0 to about 3.75. The collagen is preferably in concentrations of about 0.5 to about 1% weight/volume. The temperature at which the operations are performed is in the range of about 15° to 35° C., preferably 20°-30° C. A temperature of 22°±° C. has been observed. The dispersing or blending is performed with any suitable mechanical blending means such as a stirrer (Osterizer Blender), for a time sufficient to accomplish a thorough dispersion. Preferably the dispersion is then deaerated under appropriate vacuum like less than 0.4 millitorr. Higher and other reaction conditions can be used as discussed.

The collagen dispersion is then frozen under conditions conducive to obtaining a fibrous structure which contains pores, ideally of substantially uniform average pore size, preferably of about $100\pm50$ um, and containing channels connecting the exterior or the sponge to the inside, generally connecting one side of the product to the other, and pores that open into the channels. To obtain a very satisfactory product, the collagen dispersion is freeze-dried at a temperature range of about $-20°$ to $-35°$ C., preferably at about $-30°$ C. in a bath of a lower alkanol, like ethanol. Preferably air gaps between the sponge body and the container are minimized.

Various freezing conditions were tried from about $-20°$ C. to $-90°$ C. using an ethanol bath containing dry ice or liquid nitrogen, or other appropriate means. The frozen product (generally about at least 2 hours) is then dried, conveniently in a chamber pressure of about 0.1 millitorr at a temperature of $-60°$ C.

The cross-linking methods disclosed herein result in a stable cross-linked sponge with stable pores and channels (which show no shrinkage of the pores or the channels). The products so obtained are sponges which are characterized by porosity, consisting of pores and channels, that are interconnected. The collagen sponge so cross-linked is biocompatible, supporting the growth of fibroblasts and has a stiffness sufficient for implantation into animals in a variety of applications.

The following Examples illustrate the practice of the invention; they are not intended to be a limitation on the invention.

EXAMPLES

Materials and Methods 1. Chemicals:

All chemicals were reagent grade. D-ribose, D-glucose, DL-glyceraldehyde and D-sorbitol were obtained from Pfanstiehl Laboratories, Waukegan, Ill.

2. Glycation:

Freshly dissected tail tendons from rats weighing 200-300 g were washed briefly several times with phosphate buffered saline (PBS; 0.01 M sodium phosphate, 0.15 M NaCl, pH 7.5). Pieces of approximately 100 mg wet weight were incubated at 35° C. for defined periods of time in 2.0 ml PBS containing various sugars (D-glucose, D-ribose, D-glyceraldehyde), or D-sorbitol or without sugar as controls. A small crystal of thymol was added to each incubation mixture to prevent growth of microorganisms. Controls were not altered by prolonged incubation (more than 20 weeks) as determined by x-ray diffraction and by sodium dodecyl sulfate polyacrylamide gel electrophoresis.

3. Formaldehyde Assay for Bound Sugar:

To assay the amount of sugar bound, formaldehyde formation following periodate oxidation was measured. After incubation, the reacted tissue was washed for 30 min in several changes of PBS, reduced with 1% $NaBH_4$ w/v aqueous in PBS for 1 hr at room temperature and dialyzed against distilled water overnight. The tissue was lightly blotted and segments of tendon 10-30 mm in length were oxidized by 10 mM NaIO$_4$ in 50 mM sodium phosphate, pH 6.5, overnight in the dark at room temperature with gentle agitation. The formaldehyde released was measured spectrophotometrically (*Anal. Biochem.* 134: 499–504, 1983). One mole of attached monosaccharide was in either the Schiff base or ketoamine form assumed to produce two moles of formaldehyde upon periodate oxidation (*Anal. Biochem.* 117: 427–432, 1981). Cross-links formed between glycated ε-amino groups also released formaldehyde in the assay, at a rate of one mol of formaldehyde per mol of cross-link; cross-links formed between these ε-amino groups and other glycation products would also be expected to release formaldehyde, although yield is uncertain. Analysis of the kinetics of formaldehyde produced from glycated collagen as a function of incubation time of the protein with the aldose is consistent with the production of about 1 mol formaldehyde per mol of cross-link. The collagen content of the tissue was measured using the assay described by Berg for hydroxyproline described below, the values of monosaccharide incorporation were expressed as mols of formaldehyde released per mol of collagen α chain divided by 2.0. At short times of incubation, when the contribution from cross-links is negligible, this is equal to the number of sugars bound per α chain. The values for bound sugar obtained by this formaldehyde assay were consistent with the loss of lysine and hydroxylysine determined by amino acid analysis performed on several of the specimens.

4. Fluorescence Assay for Collagen Cross-Linkages:

Elution profiles were monitored by fluorescence recorded on a Turner Model 112 filter spectrofluorometer. Fluorescence excitation spectra in 0.01 M acetic acid were recorded on a Perkin Elmer Model MPF-3 spectrofluorometer, using an emission wavelength of 440 nm.

5. Collagen Assay:

Tissue collagen content was measured as collagen α-chain concentration employing a standard hydroxyproline assay. (Berg, *Methods in Enzymology*, Cunningham and Frederiksen, eds.; Academic Press, N.Y., vol 82, part 4, pp 372–397, 1982).

6. Collagen Extraction:

Collagen was extracted from tendon by acid, by pepsin treatment, and by CNBr digestion. About 15 mg (wet weight) of glycated tissue was finely chopped with a razor blade and extracted in 10 ml of 0.5 acetic acid at 4° C. with constant stirring overnight. Each extract was centrifuged (32,000×g for 1 h at 4° C.), and the supernatant was dialyzed against water and lyophilized to give the acid soluble fraction. The insoluble precipitate was extracted overnight with pepsin (10 μg/ml in 0.5 M acetic acid, 10 ml total volume; substrate:enzyme weight ratio about 50:1) with constant stirring at 4° C. This is referred to herein as a "standard" pepsin extraction. Following centrifugation, the supernatant was dialyzed against water and lyophilized to give the pepsin soluble fraction. The undigested precipitate obtained after pepsin treatment was lyophilized to give the insoluble material. The extractability at each step was expressed as a percentage of the sum of the acid-soluble, pepsin-soluble, and insoluble fractions.

In contrast to the standard pepsin digestion described above, a more extensive digestion at room temperature was used to cleave the telopeptides completely. One mg pepsin per 10 mg wet weight of collagen was used and the homogenate was stirred at room temperature (22° C.) for 1 day. More pepsin was added to bring the total to approximately 1 mg pepsin per 4 mg collagen and the digestion continued for another day. This room temperature treatment with a high pepsin concentration is referred to herein as "extensive" pepsin digestion.

The solubilization of glycated tendon by CNBr was carried out as follows: about 10 mg wet tissue was treated with 1 ml of 70% formic acid containing 100 mg CNBr at 30° C for 6 hr, and dried in vacuum over NaOH. After addition of 10 mM acetic acid with intensive mixing, centrifugation in an Eppendorf microcentrifuge yielded the CNBr soluble and insoluble fractions. These fractions were lyophilized and weighed.

7. X-ray Diffraction Studies:

At the end of the incubation (glycation) period, tendons were washed in PBS as above and mounted in an enclosed specimen cell over PBS with the free ends immersed in the solution, which serves to maintain the fully hydrated state. Specimens were stretched slightly to remove visible "crimp". The x-ray source was a Rigaku RU-100H rotating anode generator with a 0.1×1.0 mm focal spot operated with a copper anode at 40 kV, 20 mA. The x-ray camera used a flat film with a specimen-to-film distance of 15 cm and was equipped with a double mirror optical system. The specimen-to-film distance was calibrated by the 0.796 nm reflection of powdered beryl put on each specimen. Patterns were recorded on Kodak No-Screen or DEF x-ray film with exposure times of one to three days. To determine the meridional D period, the positions of the centers of the meridional reflections were measure on a microcomparator (Nikon Profile Projector model 6C) equipped with a micrometer stage, and the D period was calculated by linear regression. For crystalline specimens, the positions of discrete equatorial and near-equatorial reflections were measured on the microcomparator. For non-crystalline specimens, the position of the diffuse equatorial maximum was determined from a microdensitometer tracing (Joyce-Loebl). Integrated intensities of meridional reflections were obtained from microdensitometer data.

Analysis of unit cell dimensions: The apparent parameters of the collagen unit cell were determined by least-squares refinement against the positions of approximately 20 pairs of (R,Z) reciprocal space co-ordinates representing about 10 independent discrete reflections taken from each film following procedures of Fraser & MacRae (1981). It was assumed that each reflection from the slightly perturbed lattices had the same index as in native rat tail tendon.

8. Isolation of Cross-linked Collagen Chains: Collagen extracted with an extensive pepsin digestion from tendons was analyzed further by carboxymethyl cellulose (CMC) chromatography. After pepsin digestion the insoluble material was removed by centrifugation, and the solubilized collagen was precipitated with 0.7 M NaCl. The salt-precipitated collagen was collected after centrifugation and redissolved in 500 ml of 0.5 M acetic acid. The salt precipitation was repeated, the collagen was dissolved in 0.5 M acetic acid, then dialyzed against 0.06 M sodium acetate buffer, pH 4.8 (CM buffer). Pepstatin (10 βg/ml) was added to the collagen solution in CM buffer and allowed to stand overnight with constant stirring to inhibit the action of remaining pepsin. The collagen was denatured by heating at 45° C., for 30 min just before application to the column (Whatman CM-52; 1.5×10 cm) The sample was eluted with 600 ml of a linear gradient of NaCl (0 to 0.1 M in CM buffer) at 42° C. and 5 ml fractions were collected.

The elution was monitored by absorbance at 230 nm (0.01 M acetic acid, Cary model 118 spectrophotometer) and by fluorescence (see below). Fractions corresponding to each chain were pooled, dialyzed against water and lyophilized.

For further purification of soluble collagen molecules, gel chromatography on a Sepharose CL-6B column (1.5×78 cm) was performed using a 0.05 M Tris-HCl, 1.0 M $CaCl_2$ pH 7.5 buffer. The elution was followed by absorbance at 230 nm and by fluorescence (see below). Purified fractions were pooled, dialyzed against water and lyophilized.

For CNBr digestion of chains following chromatography, about 10 mg of lyophilized collagen was dissolved in 1 ml of 70% formic acid. One hundred mg CNBr was added and the mixture was held at 30° C. for 4 hours. The peptides were dried in vacuum over NaOH, redissolved in 10 mM acetic acid and lyophilized.

9. Characterization of Cross-linked Collagen Chains:

Tendon from a three month old rat was incubated in 0.2 M ribose for 2 days and then exposed to an extensive pepsin digestion. The solubilized collagen was purified by salt precipitation and the collagen chains were partially separated on CMC chromatography (FIG. 5) The elution was monitored both by absorbance and by fluorescence. The pepsin resistant dimers eluted at the same salt concentration as expected for native 11, 12, and 22 components (FIG. 5) and a high value of specific fluorescence was associated with these three beta fractions. The relative ratio of specific fluorescence was approximately 1:3:0.5 for the $\beta 11:\beta 12:\beta 22$ fractions.

All three dimers showed a large amount of HM-CNBr peptides which was not found for $\beta 11$, $\beta 12$, and $\beta 22$ from untreated young rat tail tendon collagen and not found for the ribose treated $\alpha$ chains (data not shown). Each dimer type showed a characteristic HM-CNBr pattern containing two or three strong bands superimposed on a diffuse background.

The CMC absorbance profile for an extensive pepsin digest of control young tendon incubated in PBS without ribose was similar to that seen for glycated tendon, but the fluorescence levels were very low (data not shown). For example, the $\beta 12$ fluorescence was at the most 10% of the values recorded for the glycated collagen.

10. Collagen Purification:

Type I collagen (Devro Inc., Somerville, N.J.) from bovine hide was purified by sequential washing. One liter of raw material was placed in a drum with 8 liters of distilled water. The material was then agitated by bubbling air through the solute and the water removed. The next stage involved washing in 4 liters of isopropanol to dissolve residual lipids and fats. Treatment lasted 48 hours with 2 changes of isopropanol. The final stage involved washing in 4 liters of distilled water. The water was removed, the material frozen and lyophilized.

11. Collagen Dispersion Preparation:

A 1 N solution of HCl was added 120.0 ml of distilled water until the pH was 2.0. A 0.9 gram sample of purified type I collagen was put into a blender (Osterizer Corp., Milwaukee, Wis.) along with the 120.0 ml of the HCl solution pH 2.0. This 0.75% w/v collagen HCl dispersion was then emptied from the blender into a 600 ml sidearm flask. A vacuum of 100 microns was applied at room temperature until the air bubbles were removed from the dispersion. This procedure required approximately 15 minutes. The vacuum was removed and the dispersion was used for sponge preparation.

12. Collagen Sponge Preparation:

For sponge preparation, 60 ml of the dispersion prepared according to the method described above was poured into a metal pan, spread evenly within the pan, and then placed in a freezer at −80° C. until frozen solid. The frozen material was then lyophilized at 0° C. Sponges prepared in the above manner were then ready for cross-linking treatment.

13. Cross-linking Procedures for Collagen Sponges:

a. Dehydrothermal Cross-linking:

Collagen sponges were placed in a vacuum over 25° C. and subjected to a vacuum of 100 microns for 1 hour. The temperature of the oven was then increased to 110° C. Treatment lasted for 3 days. The oven temperature was then reduced to below 50° C., and the samples removed.

b. Carbodiimide Cross-linking:

Collagen sponges were immersed in a 1% solution of cyanamide (pH 7.4) for 0 to 110 hrs at room temperature. The sponges were then removed and washed in water for 2 days. Water was changed 5 times over the 2 day period to insure complete washing. The sponges were then frozen and lyophilized (Weadock et al, *Biomater. Med. Devices Artif. Organs,* 11, 293–318, 1984).

c. Carbohydrate Cross-linking:

Collagen sponges were immersed in a 0.2 M solution of ribose in phosphate buffered saline (pH 7.4) for 0 to 110 hours at room temperature. The sponges were then removed and washed in water for 2 days to remove any residual carbohydrate. The water was changed 5 times to insure complete washing. The sponges were then frozen lyophilized. 10 d. Fibroblast Cell Cultures:

Freshly isolated fibroblasts were obtained-using the method described by Kao et al, *Biochem. Biophys. Acta,* 411, 202 (1975). Leg tendons were removed from 17-day old chick embryos by dissection and cells were isolated from the tendons by digestion under controlled conditions using bacterial collagenase and trypsin. Fibroblasts derived from embryonic chick tendons were suspended in medium at a concentration of 10 per ml in Dulbecco's Modified Eagle Medium (DMEM) (Gibco, N.Y.) supplemented with 100 units/ml penicillin, 100 ug/ml streptomycin, 10 ug/ml ascorbic acid added daily and 5% fetal bovine serum. The collagen sponges were equilibrated for three days by immersion in serum free DMEM to allow any residual acid to diffuse from the sponge. For mechanical studies, fibroblasts were plated on collagen sponges at a concentration of 2 million cells/cm in aliquots of either 1 ml or 0.2 ml and allowed to attach for 1 hr prior to adding the remaining 3 ml of culture medium to seed the sponges. Cells were grown at 37° C. in a tissue culture incubator in a 10% CO, 90% air atmosphere for 7 and 21 days.

Results

1. Glycation and Cross-link Formation by Monosaccharides:

Since the rate of glycation depends on the concentration of the acyclic aldehydo form of the sugar in solution, the incorporation of three monosaccharides, glucose, ribose and glyceraldehyde, which respectively manifest approximately 0.002%, 0.05%, and 100% relative concentration of the open chain form were measured. Rat tail tendons were incubated at 35° C. in various concentrations of these sugars and after specified times the tendons were assayed for bound sugar (formaldehyde assay) as a measure of glycation. The results are shown in FIG. 1. The reaction with glucose was quite slow, that with ribose was of intermediate rate, and the reaction with glyceraldehyde was very rapid; about one ribose moiety per α-chain was bound after 5 days incubation, whereas only one glucose moiety was bound after 8 weeks. Incubation with sorbitol, a nonreactive control, showed no incorporation of sugar.

Figure 2:
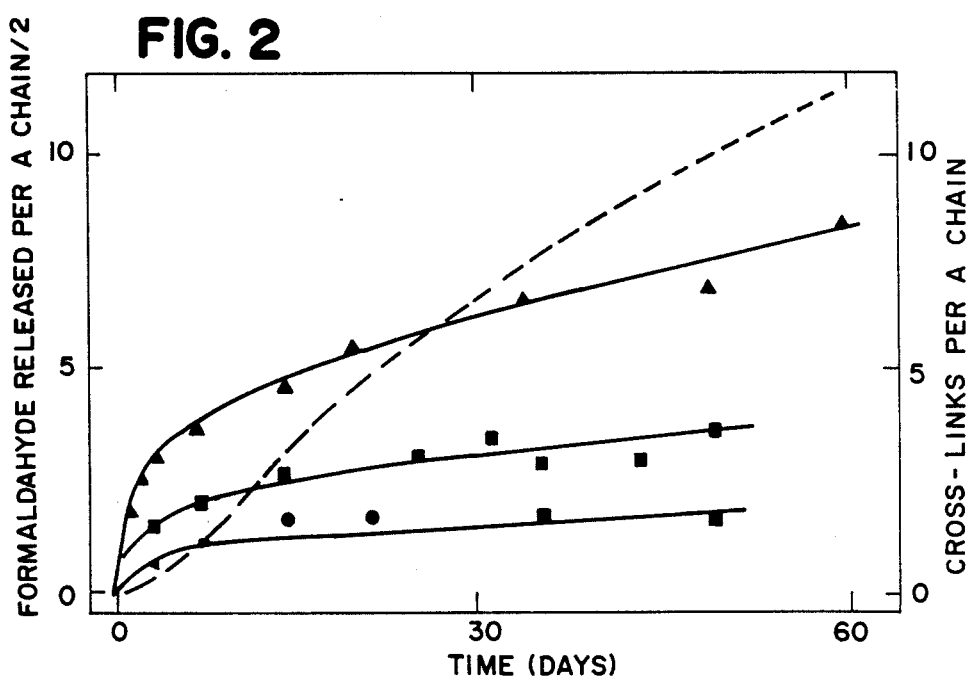
FIG. 2.—Glycation of rat tail tendon by ribose at various concentrations. The left ordinate is as in FIG. 1.
Symbols: (▲), 0.2 M D-ribose; ( ), 0.1 M D-ribose; (●), 0.05 M D-ribose. The differential equations (see text) describing the model in FIG. 3 were solved numerically using an initial value for C of 33.7 $\delta$-amino groups per $\alpha$ chain (average of two $\alpha$1 and one $\alpha$2 chains) and a value for Y of 1.0. The possible contribution of the $\alpha$-amino group was ignored. The best-fit values of the rate constants were: $k_{+1} = 0.58$ $M^{-1}$ day, $k_{-1} = 0.42$ day$^{-1}$, and $k_2 = -0.024$ (groups per $\alpha$ chain)$^{-1}$ day$^{-1}$. The root mean square residual error was 0.28 (using the units of the ordinate) and the fit of the model to the data was statistically acceptable at the 95% level of confidence. The three parameters are highly covarient; so, their individual values should be taken only as approximations and not used to extrapolate beyond the present data. The solid lines represent the values predicted by the model using the best-fit values of the rate constants. The broken line represents the concentration of cross-links, X, formed according to the model for incubation with 0.2 M ribose.

Incubation of tail tendon from a 3 month-old rat with 0.05 M, 0.10 M and 0.2 M ribose showed a strong dependence on the concentration employed. As shown in FIG. 2, the extent of ribose binding as measured by formaldehyde release on periodate oxidation increased with sugar concentration and the reaction manifested complex kinetics, comprising an initial rapid reaction with a time constant of a few days followed by a much slower reaction which did not plateau during the period investigated; the kinetic data were consistent with a reversible binding of sugar to collagen, followed by the irreversible formation of cross-links. Glycation was accompanied by a decreased extractability of the collagen, which indicates the formation of intermolecular cross-links. Control experiments demonstrated that the biphasic appearance of the glycation kinetics did not result from a contaminant in the ribose solutions, a situation that has been reported for glucose.

Chase experiments (data not shown) with radiolabeled ribose indicated that part of the ribose non-enzymatically attached to the protein was releasable. Previous work with glucose indicates that the aldimine form is readily hydrolyzed, whereas the ketoamine adducts of glucose and glyceraldehyde bound to ε-amino groups is at most slowly hydrolyzed. A large proportion of the unreleased ribose was apparently incorporated into cross-link structures between chains over a period of five days, as indicated by the high specific radioactivity of separated HM-CNBr fragments, which represented dimers or oligomers of peptides joined by such sugar-derived cross-links.

A mathematical model (not shown) was developed for these glycation kinetics, especially the variations in the rates of reaction and non-linear dependence of the asymptotic rate on sugar concentration. The broken line in FIG. 2 shows the production of cross-link material according to this model using the best-fit values of the rate constants. It is seen that in 0.2 M ribose, cross-links are produced at the rate of about one per α chain every five days, and that over the first two to three weeks, the production of cross-links is approximately linear with time. The rate of cross-link formation has a non-linear dependence on sugar concentration; reducing the ribose concentration to 0.1 M increases the time to form one cross-link to about 13 days. The kinetic data are consistent with a reversible binding of sugar to collagen followed by the irreversible formation of cross-links.

Figure 3:
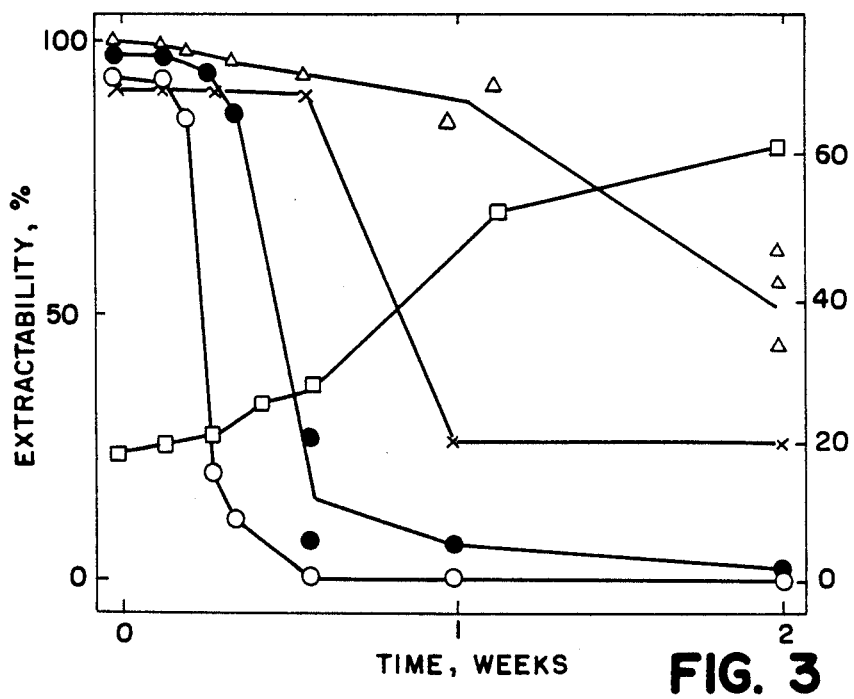
FIG. 3.—The extractability of collagen from rat tail tendon by 0.5 M acetic acid ( O ), by a mild digestion with pepsin (●), by an extensive room temperature pepsin digestion (X), and by CNBr (▲) as a function of incubation time with 0.2 M ribose. Also shown is the fluorescence intensity (■) of the fraction solubilized by CNBr treatment. The fluorescence values were normalized by the $A_{230}$ of the fractions.
Figure 11:
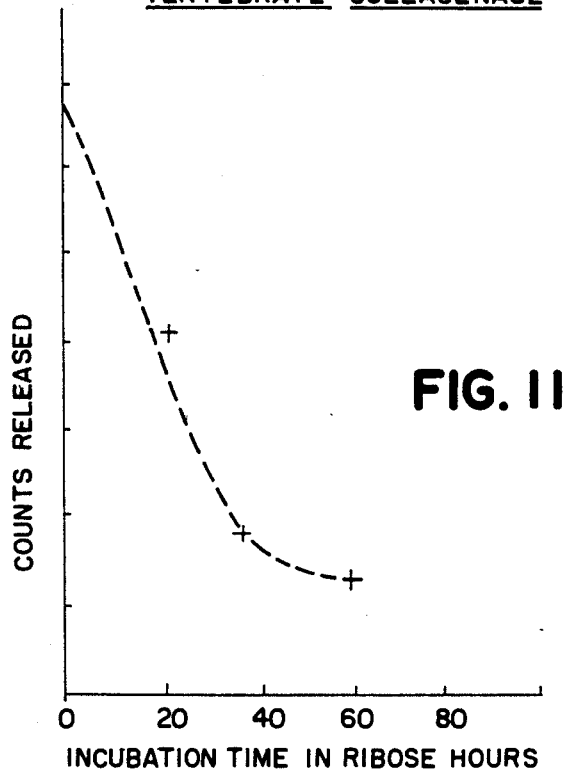
FIG. 11—Shows that incubation of rat tail tendon in ribose makes it less susceptible to digestion by vertebrate collagenase.

We have omitted the mathematical model and used the simpler $k_1$, $k_2$, values of your FIG. 3. The numerical value of $k_1$ was taken from the hemoglobin reactions of Bunn and Higgins in the Science 213: 222, 223 paper. Bunn et al do not describe $k_2$, however, and we have ascribed k values that need your attention.

2. Extractability of Sugar-cross-linked Collagen:

Incubation of rat tail tendon in 0.2 M ribose greatly decreased the solubility of collagen (FIG. 3). After 2 days of incubation, the collagen was insoluble in 0.5 M acetic acid whereas the collagen from control tendons incubated at 35° C. in PBS was completely soluble. A total loss of solubility occurred after four days incubation when assayed using a standard pepsin digestion. After an incubation period of one week, an extensive pepsin digestion at room temperature solubilized only 20% of the collagen and extractability by CNBr was appreciably reduced. The extractability of the collagen dramatically decreased over incubation time, and the specific fluorescence of the extracted CNBr peptides was elevated with increasing incubation time, concomitant with the decrease in collagen solubility (FIG. 3).

In order to study the chains cross-linked specifically as a result of incubation with sugar, elimination of covalently cross-linked dimers and oligomers naturally present in control young tendon collagen was carried out. A standard pepsin digestion of young native rat tail tendon (substrate: enzyme weight ratio of 50:1 at 4° C.) leaves intact some collagen dimers which are presumably cross-linked via a telopeptide. We have found that the use of a higher pepsin concentration (substrate: enzyme weight ratio of about 4:1) at room temperature results in cleavage and extraction as monomers of almost all the collagen from a 3 month old rat tail tendon, while causing minimal degradation of the a-size triple-helix. In comparison, an extensive pepsin treatment of tendon after incubation with ribose yielded a considerable amount of dimers and oligomers in addition to monomeric peptides, and the relative proportion of higher molecular weight species to monomers increased in direct relationship with incubation time with ribose. Since the extensive enzymic digestion at room temperature appears to remove telopeptides, oligomers resistant to digestion are likely to contain the sugar mediated cross-linked structures formed between triple-helical domains of type I collagen molecules.

3. X-ray diffraction:

X-ray diffraction results demonstrated that glycation of a three dimensional array of collagen represented by rat tail tendon expands the spacing between adjacent protein molecules and eventually disrupts the crystalline molecular packing of collagen in the fibrils.

Medium-angle x-ray diffraction patterns were recorded on tendons after incubation with monosaccharides, followed by removal of the unbound sugar. The equatorial and near-equatorial spacings, and incoherent diffuse scattering along the equator and the intensities of the meridional reflections were altered by incubation with ribose, glucose or glyceraldehyde. Control tendons incubated for up to five months in PBS or for six weeks in 0.2 M-sorbitol were unaffected.

Incubation of rat tail tendon in 0.2 M-ribose led to increases in the real space positions of the equatorial and near-equatorial Bragg reflections that are derived from the crystalline unit cell of this collagen, indicating an expansion of the structure. These changes were apparent after two days of incubation, and the positions of all lattice reflections gradually and continuously became greater at various rates as the exposure time to ribose increased (FIG. 8; Table I). Unlike the complex kinetics of sugar binding, all measures of structural change exhibited essentially linear kinetics. With increasing time of incubation, the breadths of the equatorial and near-equatorial reflections increased, and there was an increase in intensity of the diffuse scattering underlying the lattice reflections, indicating a gradual loss of long-range lateral order in the structure. The x-ray patterns changed uniformly with time and showed no evidence of a superposition of patterns that would be expected to result from a mosaic structure produced by a diffusion-limited reaction. Lattice reflections were observed for incubations in ribose up to 20 days, after which only the single, diffuse equatorial maximum remained. With further incubation, the real space position of this maximum continued to increase, indicating that the expansion process continued even through long-range order had been lost.

Figure 8:
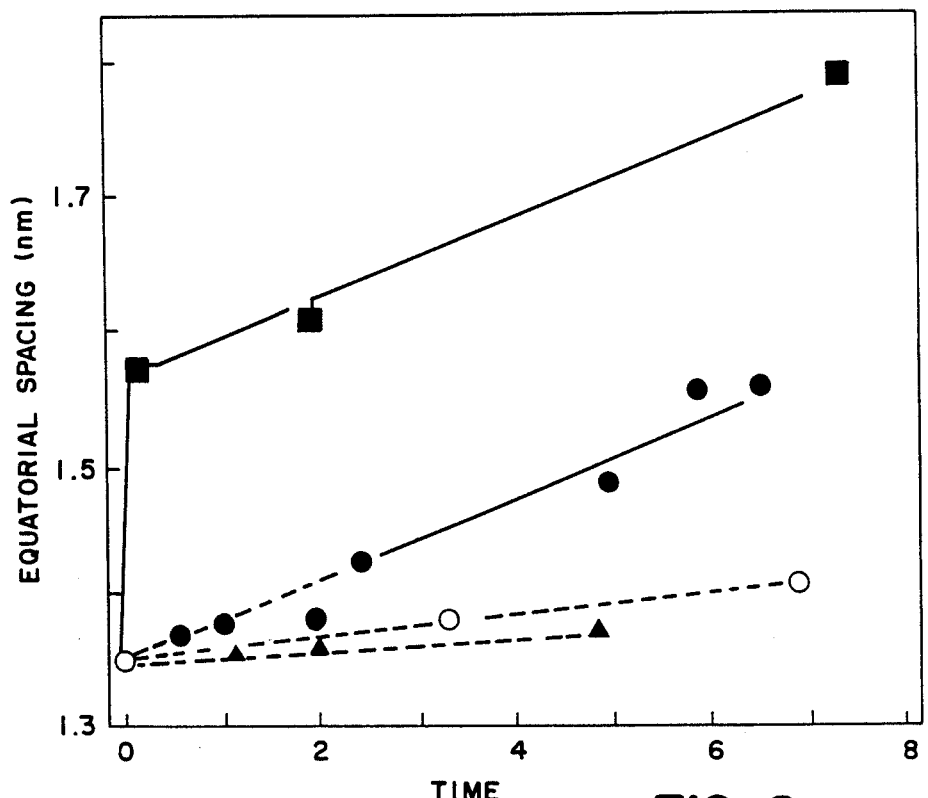
FIG. 8—Changes in equatorial spacings in rat tail tendon as a function of incubation time with various sugars. (●) 0.20 M-ribose; ( O ) 0.05 M-ribose; (■) 0.20 M-glyceraldehyde, shown with a time-scale of weeks; (▲) 0.20 M-glucose, shown with a time-scale of months. For crystalline specimens, the average of the 310, 120 and 210 equatorial reflections is plotted with a broken line. For non-crystalline specimens, the average of the 310, 120, and 210 equatorial reflections is plotted with a broken line. For non-crystalline specimens, the position of the maximum of the single broad reflection is plotted with a continuous line. Thus, in 0.2 M-ribose, discrete equatorial maxima were visible until 2–5 weeks (broken line) after which only a single broad maximum was observed (continuous line).

The changes in the lattice dimensions can be seen in the representative 310, 120 and 210 and reflections (FIG. 8; Table I), which are derived from the three main intermolecular planes of the quasi-hexagonal structure. These results indicate an apparently continuous enlargement of the unit cell of the collagen crystalline packing brought about by the glycation reaction. Table II shows the parameters of the unit cell as a function of ribose treatment that were obtained by least-squares refinement using about 20 values of reciprocal space coordinates, R and Z, taken from each film. The values obtained show that the unit cell enlarges in both lateral dimensions concomitantly with increasing levels of glycation, but by different amounts along each axis, such that the expansion is directed almost parallel to the (120) planes. Over 17 days of exposure of 0.2 M-ribose, the interaxial angle in the basal plane widened slightly, from 104.7° to 106.1°, and the cross-sectional area of the unit cell increased by about 12%.

Different concentrations of ribose and of other sugars showed effects similar to those described above, but on a timescale concomitant with the concentration of free aldehyde. Exposure of rat tail tendon to 0.05 M-ribose resulted in a slower rate of structural change than found with 0.2 M-ribose, with discrete reflections being retained even after six weeks incubation (FIG. 8). Incubation with 0.2 M-glucose resulted in a very slow rate of change, such that five months' exposure had about the same effect as four days' exposure to ribose at the same concentration (Table I; FIG. 8). In contrast, tendon incubated with 0.2 M-glyceraldehyde for one day produced a single diffuse equatorial scattering maximum, a manifestation of its much faster rate of reaction.

TABLE I

Positions of the discrete equatorial and near-equatorial intensity maxima in the x-ray diffraction pattern of rat tail tendon after incubation with monosaccharides for different times.

| Sugar solution | Incubation time | | Row line spacing (nm)+ | | | |
|---|---|---|---|---|---|---|
| | | | 310 | 120** | 210 | 100 |
| Control (without sugar) | 0 day | | 1.28 | 1.38 | 1.40 | 3.83 |
| | 5 months | | 1.30 | 1.37 | 1.39 | 3.87 |
| 0.05 M-ribose | 24 days | | 1.33 | 1.40 | 1.43 | 3.95 |
| | 49 days | | 1.37 | 1.41 | 1.45 | 4.13 |
| 0.20 M-ribose | 4 days | | 1.31 | 1.39 | 1.41 | 3.94 |
| | 14 days | | 1.34 | 1.40 | 1.43 | 4.00 |
| | 17 days | | 1.39 | 1.44 | 1.46 | 4.42 |
| | 35 days | 1.49 f | | | | |
| | 45 days | 1.56 f | | | | |
| 0.20 M-glucose | 1 month | | 1.29 | 1.38 | 1.39 | 3.87 |
| | 2 months | | 1.30 | 1.38 | 1.40 | 3.88 |
| | 5 months | | 1.32 | 1.38 | 1.41 | 3.92 |
| 0.20 M-glyceraldehyde | 1 day | 1.57 f | | | | |
| | 14 days | 1.61 f | | | | |
| | 52 days | 1.80 f | | | | |

Up to 7 near-equatorial reflections could be indexed on crystalline patterns. The 4 most prominent are listed here.
**The 120 and 210 reflections are difficult to separate on the microcomparator. Therefore, values for these 2 reflections were calculated assuming the size of each individual reflection is the same as that measured for the 310 reflection.
f Discrete lattice reflections were replaced by a single broad equatorial maximum.

+Up to 7 near-equatorial reflections could be indexed on crystalline patterns. The 4 most prominent are listed here.

** The 120 and 210 reflections are difficult to separate on the microcomputer. Therefore, values for these 2 reflections were calculated assuming the size of each individual reflection is the same as that measured for the 310 reflection.

f Discrete lattice reflections were replaced by a single broad equatorial maximum.

TABLE II

Changes in the unit cell of the rat tail tendon collagen upon incubation in 0.2 M-ribose

| Unit cell parameter | Native rat tail tendon+ | Time of incubation (days) | | | |
|---|---|---|---|---|---|
| | | 0 | 4 | 14 | 17 |
| a (nm) | 3.997 | 3.958 | 4.037 | 4.113 | 4.288 |
| b (nm) | 2.695 | 2.748 | 2.770 | 2.787 | 2.872 |
| c (nm) | 67.79 | 67.30 | 67.37 | 67.28 | 67.25 |
| a (deg.) | 89.24 | 89.04 | 89.47 | 89.10 | 88.31 |
| B (deg.) | 94.59 | 93.36 | 93.31 | 92.61 | 92.43 |
| (deg.) | 105.58 | 104.31 | 104.94 | 105.11 | 106.15 |
| Standard spacing alone 120 in the ab plane (nm) | 1.544 | 1.542 | 1.566 | 1.594 | 1.650 |
| Area (nm$^2$) | 10.40 | 10.54 | 10.80 | 11.07 | 11.83 |
| Relative volume | — | 1.000 | 1.025 | 1.050 | 1.122 |

+Fraser et al. (1983)

4. Isolation and Characterization of Cross-linked Dimers:

To characterize the cross-linked collagen, oligomers with gel electrophoretic mobility in the region were isolated from ribose cross-linked tendon. The use of an extensive room temperature pepsin digestion largely eliminated native oligomeric chains linked through telopeptides, thus allowing substantial enrichment of dimers resistant to digestion containing the sugar-mediated cross-linked structures formed between triple-helical domains of the type I collagen molecules.

Figure 4:
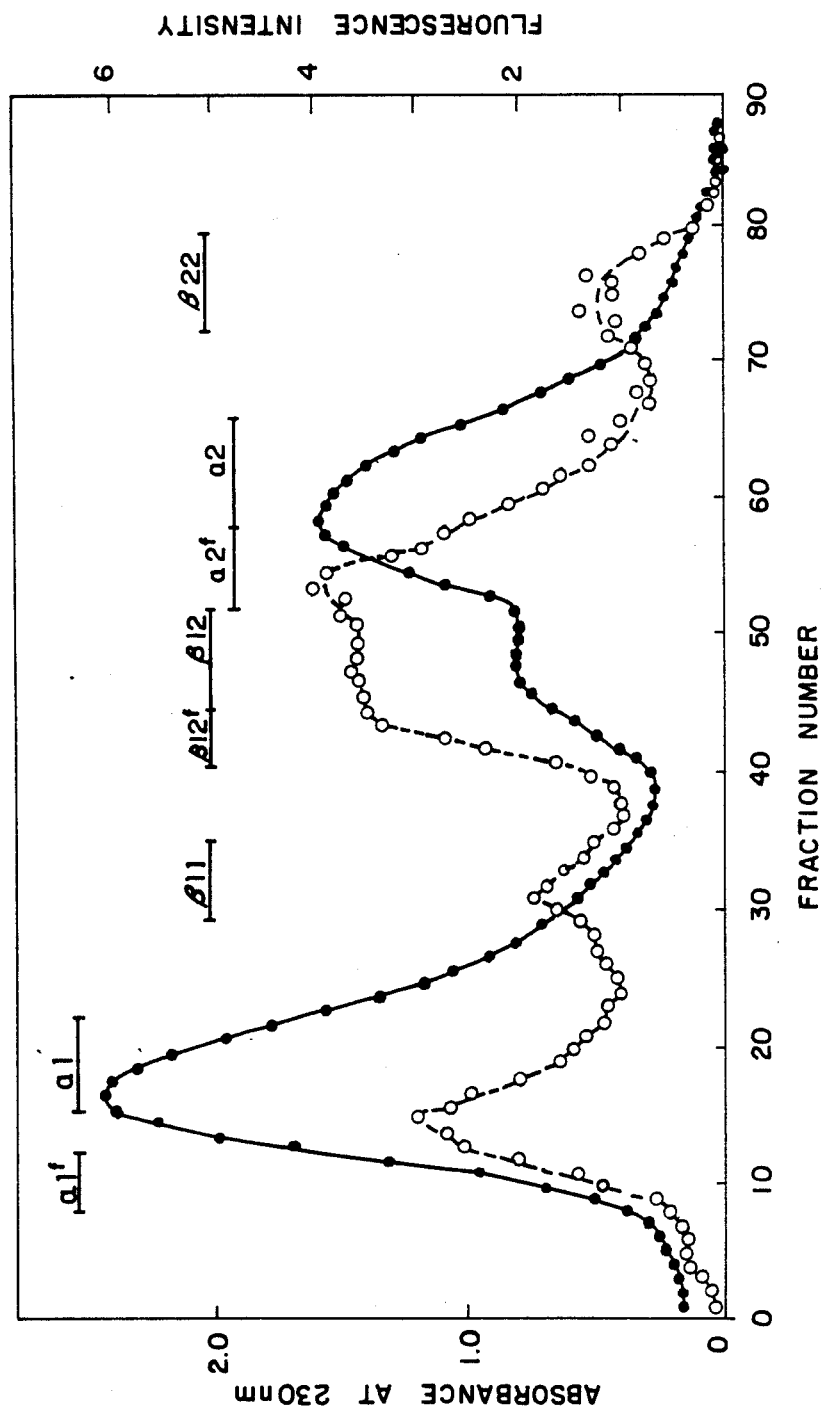
FIG. 4.—CMC-chromatography of material extracted by extensive pepsin treatment of tendon incubated for 2 days in 0.2M ribose. The elution was monitored by A230 (●) and by fluorescence intensity, arbitrary units ( O ). The bars indicate the fractions gathered. Where one peak is separated into two sets of fractions, the superscript "f" is used to designate the leading fraction.

Tendon from a three month old rat was incubated in 0.2 M ribose for 2 days and then exposed to extensive pepsin digestion. After the two day incubation with ribose, three kinds of pepsin-resistant β chains were isolated from the solubilized collagen by fluorescence and absorbance monitored chromatographic separation and identified by their CNBr peptide patterns as dimers containing two α1 chains (β11), one α1 chain and one α2 chain (β12) and two α2 chains (β22); a high value of specific fluorescence was associated with these three beta fractions (cf. FIG. 4). The relative ratio of specific fluorescence was approximately 1:3:0.5 for the β11: β12 β22 fractions. The CMC absorbance profile for an extensive pepsin digest of control young tendon incubated in PBS without ribose was similar to that seen for glycated tendon, but the fluorescence levels were very low (data not shown). For example, the $\beta 12$ fluorescence was at most 10% of the values recorded for the glycated collagen.

To purify further these pepsin resistant dimers the $\beta$ and $\alpha$ fractions from CMC column were subjected to Sepharose CL-6B gel filtration column chromatography. The $\alpha 1$, $\alpha 2$, $\beta 11$, $\beta 12$ and $\beta 22$ fractions obtained from a tendon incubated for 2 days in ribose and purified by CMC followed by Sepharose CL-6B chromatography were examined on SDS-PAGE (not shown). The $\alpha 1$ and $\alpha 2$ fractions had normal mobilities, indicating the amount of sugar attached was too small to affect peptide migration rate. Each $\beta$ fraction showed a characteristic set of two or three discrete bands superimposed on a diffuse background, and the mobility of the $\beta 22$ material was anomalously slow. The presence of multiple $\beta$ bands and the anomalous mobility may be accounted for by either the presence of cross-links at different sites in dimers or the attachment of small residual peptides.

Figure 5:
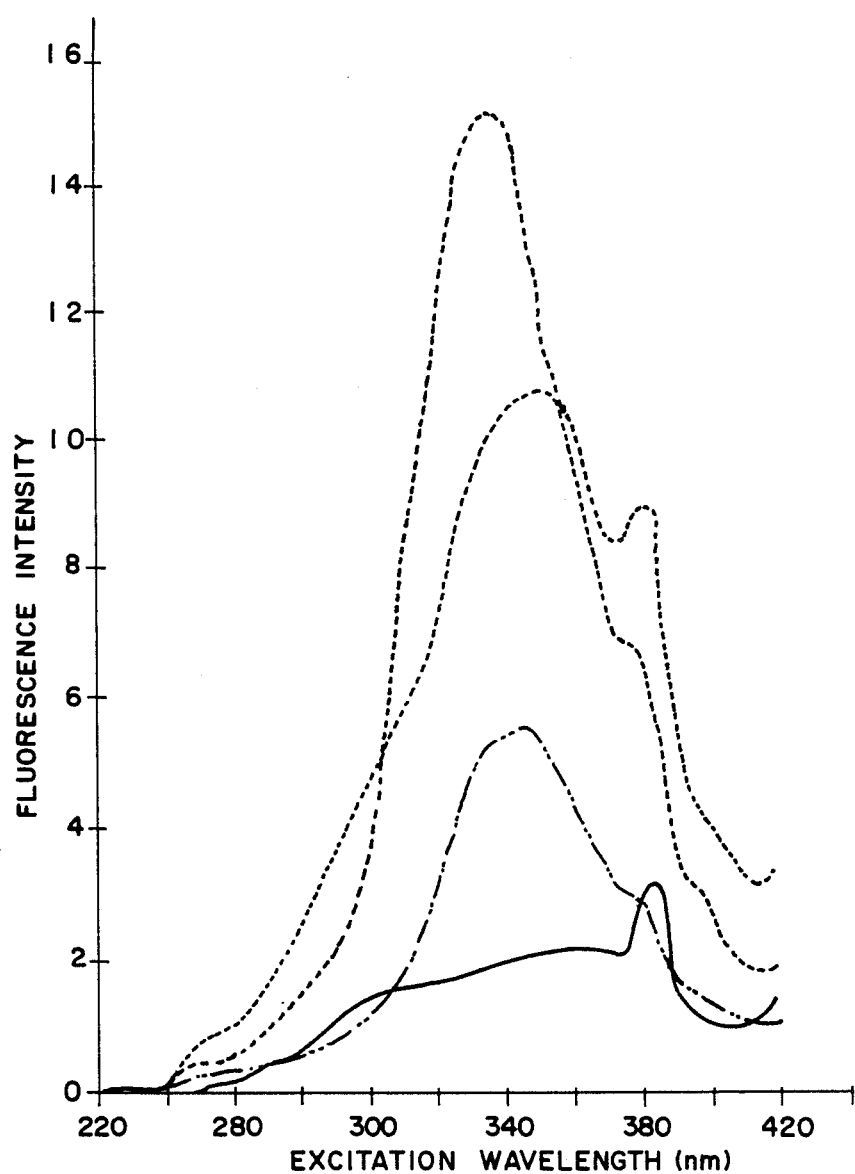
FIG. 5.—Fluorescence excitation spectra of collagen chains isolated after extensive pepsin treatment using an emission wavelength of 440 nM (---), $\beta12$ from young tendon after 2 ribose treatment; (...), $\alpha1$-f from young tendon after 2 day ribose treatment; (--.--), $\beta12$ from a 15 month old tendon; (---), $\alpha1$ from a 15 month old tendon. The fluorescence intensity is given in arbitrary units, normalized to the protein concentration monitored by A230.

The fluorescence excitation spectrum of purified pepsin-resistant $\beta 12$ dimers from tendon incubated in ribose showed a maximum near 340 nm using an emission wavelength of 440 nm (FIG. 5). An emission maximum near 445 nm (with an excitation wavelength of 370 nm) appeared in these $\beta 12$ components (data not shown). This is compatible with the fluorescence spectrum profile of the cross-linking collagen chromagen reported in *Proc. Natl. Acad. Sci.* 81: 583–587 (1984). The fluorescence peak which eluted at the leading edge of $\alpha 1$ by CMC chromatography has an excitation maximum similar to that of the $\beta$ components but with a lower specific activity (FIG. 5); Sepharose CL-6B gel filtration chromatography confirmed that the fluorescence was associated with the $\alpha$ chain (data not shown).

EXAMPLE II

Preparation of Cross-linked Collagen Sponges and Comparison of Stiffness and Biocompatibility:

A. Collagen sponges were prepared as described in the *Methods* section and cross-linked with ribose (RB), with cyanimide (CI) or by dehydrothermal (DHT) treatment. The DHT sponges were compared to carbodiimide cross-linked sponges (CI sponges) and ribose cross-linked sponges (RB sponges) with respect to stiffness in absence of fibroblasts and in presence of cells (composite sponges) over time. All sponges were sterilized after cross-linking by irradiation at 2.5 M rad to prepare them for cell culture. The sponges were either unseeded with cells (controls) or seeded with cells and incubated for 7 or 21 days at 37° C. with 5% $CO_2$ atmosphere.

Figure 6:
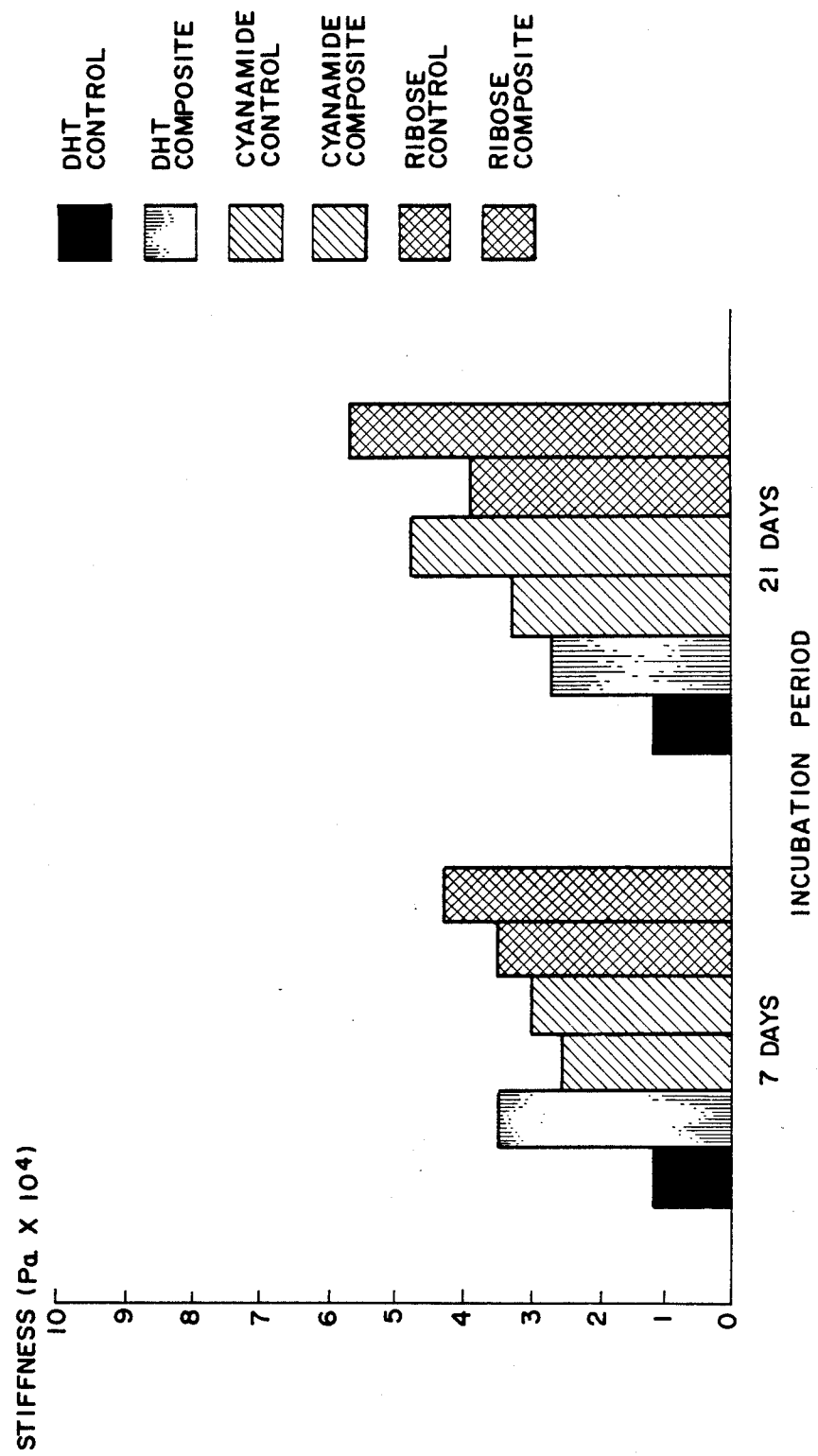
FIG. 6—Illustrates the effect of various cross-linking procedures on properties of collagen matrices.

The results of the experiments are illustrated in FIG. 6 and the following Table. Each bar in the graph represents an averaging of 7 samples. The Table reports the number of cells present after specified number of days in culture. DHT cross-linked sponges had the lowest stiffness (modulus), followed by CI sponges. RB sponges had the greatest stiffness in both seeded ("composite") sponges and unseeded ("control") sponges. The RB sponges showed excellent biocompatibility and promotion of cell ingrowth.

The mechanical properties of these strips were analyzed with an Instron tester model 1122 in a hydrated state by uniaxial tensile testing at room temperature using a constant strain rage. The strips were placed between pneumatic grips (40 psi) and a gage length of 10 mm and constant cross-head speed was set. Stress-strain curves obtained by this analysis were used to calculate Young's modulus in both the low and high strain regions. Strain was defined as the change in length over initial length, stress as the force divided by the cross-sectional area, Young's modulus as the change in stress over change in strain, and ultimate tensile strength as the stress at failure. Young's modulus was found by calculating the initial slope of the stress-strain curve in the linear region.

TABLE

| Cell growth on Cross-linked Collagen Sponges: Biocompatibility | | |
|---|---|---|
| Treatment | Days in culture | Total Cells/2 $cm^2$ |
| DHT | 0 | $1.5 \times 10^6$ |
| DHT | 7 | $2.0 \times 10^6$ |
| DHT | 21 | $3.3 \times 10^6$ |
| Cyanimide (CI) | 0 | $1.5 \times 10^6$ |
| Cyanimide (CI) | 7 | $2.2 \times 10^6$ |
| Cyanimide (CI) | 21 | $6.9 \times 10^6$ |
| Ribose (RB) | 0 | $1.5 \times 10^6$ |
| Ribose (RB) | 7 | $4.2 \times 10^6$ |
| Ribose (RB) | 21 | $10.0 \times 10^6$ |

B. Collagen sponges were prepared as described under "Methods". The sponges were cross-lined by (a) immersion in 1% cyanimide solution (b) immersion in a 0.2 M solution of D-ribose in distilled water, (c) immersion in a 1 M solution of D-ribose in distilled water, for varying lengths of time.

Stiffness (modulus) was determined as set forth in Example II, "A", above.

Figure 7A:
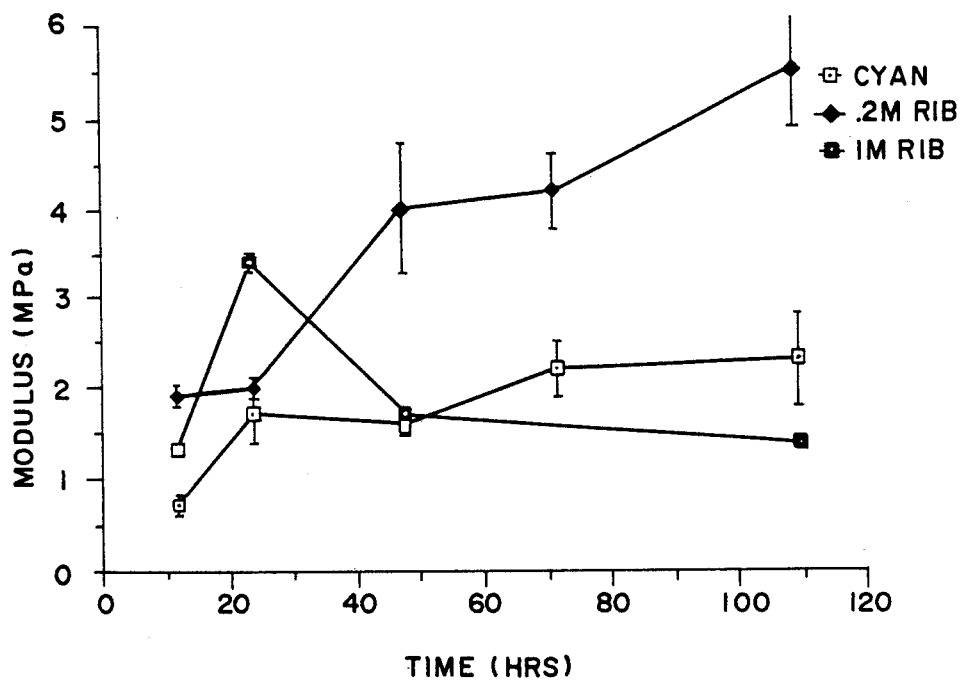
FIG. 7.—Collagen sponges prepared according to the Examples were incubated for various lengths of times with either cyanamid, 0.2 M ribose or 1 M ribose. The matrices were then examined by mechanical testing for stiffness (modulus) (FIG. 7a) or ultimate tensile strength (UTS) (FIG. 7b).

The data in FIG. 7a indicate that the modulus is increased significantly with ribose cross-linking, and continues to increase even beyond 40 hours with 0.2 molar ribose. 1 molar ribose was not effective for cross-linking the matrix to determine the mechanical properties. It is theorized that increased concentration of ribose may cause free ribose to interact with glycated collagen and disrupt the collagen architecture. Additionally 1 M ribose was quite viscous and the matrix geometry and pore structure was altered. At lower concentrations of ribose the matrix geometry was preserved.

Figure 7B:
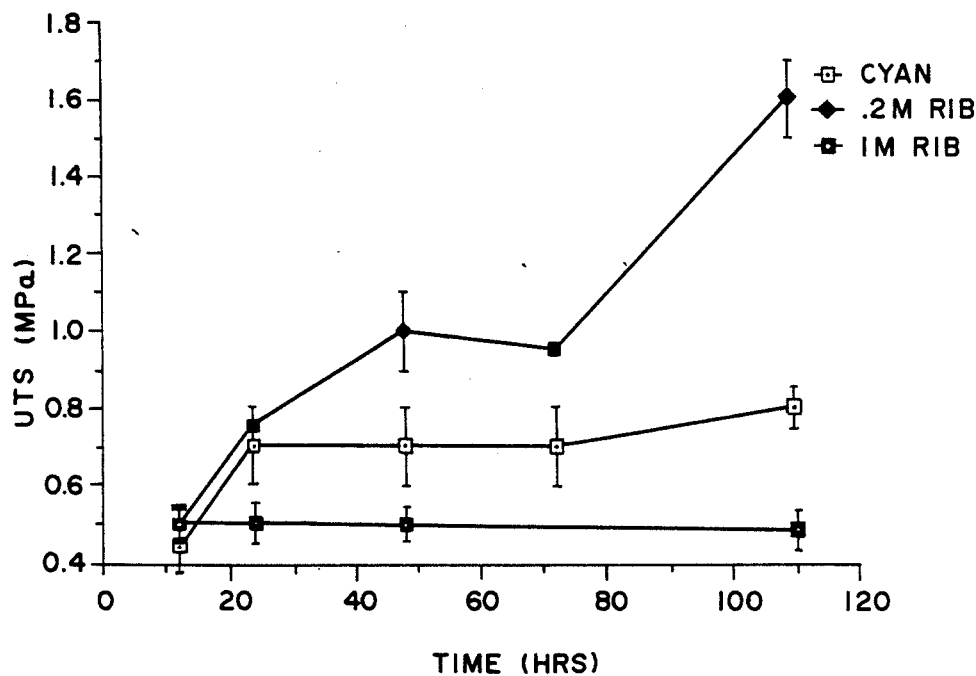
Figure 9A:
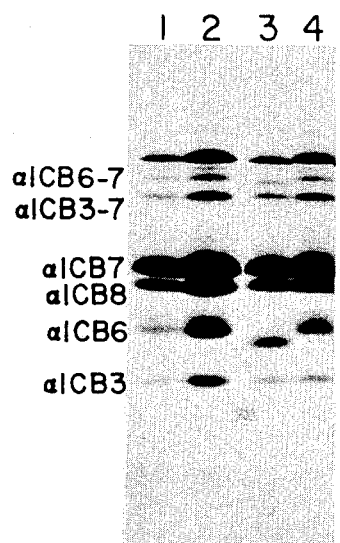
FIG. 9(a–d)—Show SDS-PAGE (12.4% gel) of CNBr digests of rat tail tendon labeled by incubation in [$^{14}$C] ribose.
Figure 9B:
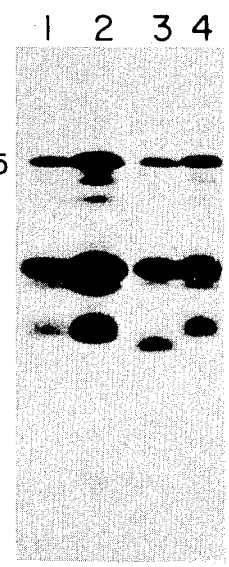
Figure 9C:
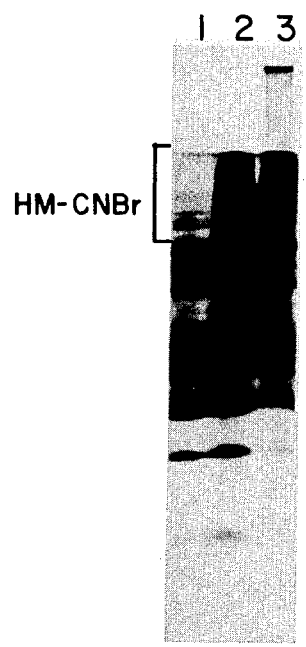
Figure 9D:
Figure 10:
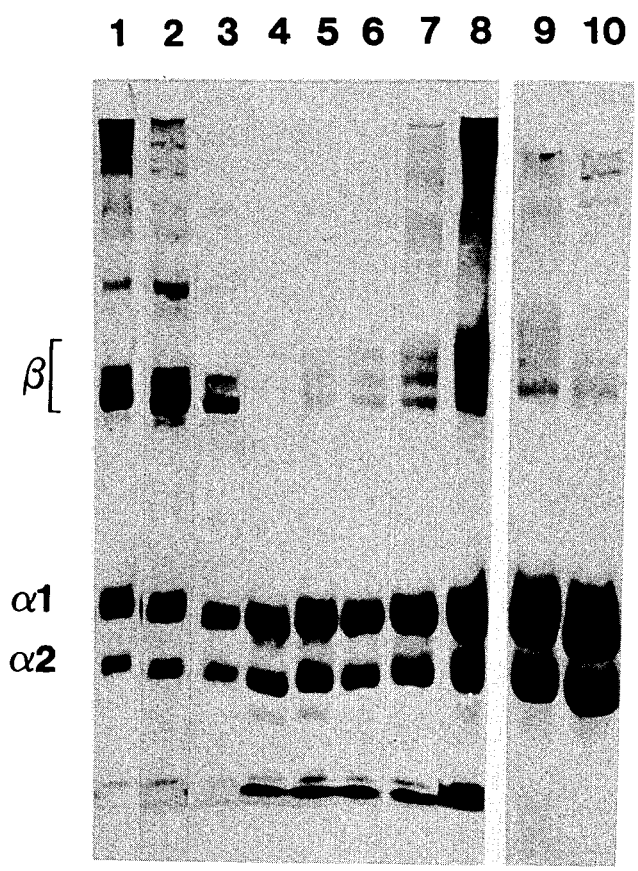
FIG. 10—Shows SDS-PAGE (4.5% gel) of collagen extracts from rat tail tendon after incubation with or without 0.2 M ribose.
Figure 12:
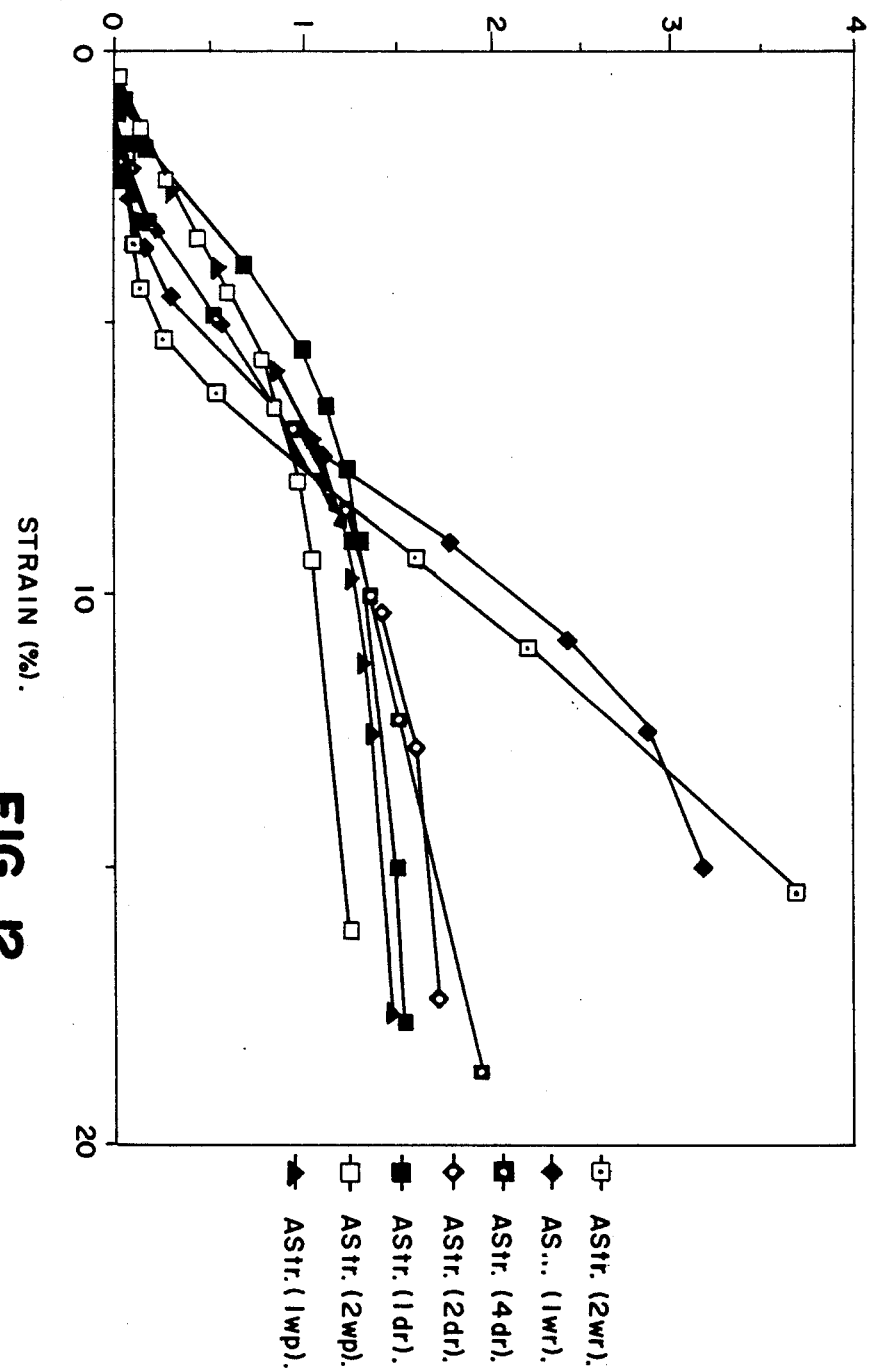
FIG. 12—Shows that incubation of rat tail tendon in 0.2 M for one week (●) and for two weeks ( o ) increases the tensile strength of the tendon.

When the ultimate tensile strength was examined for these sponges crosslinked by cyanimide or ribose it was again found that 0.2 molar ribose provided the optimal crosslinking compared with either 1 molar ribose or the cyanamid treatment of the sponges (FIG. 7b). This data is consistent with the data in FIG. 7 on the modulus and indicates that the sponges cross-linked with ribose are effectively cross-linked to change the mechanical properties.

The references listed below of interest as background to the invention are incorporated herein by reference. Also incorporated is a publication entitled Glycation Induces Expansion of the Molecular Packing of Collagen, by Shizuko Tanaka, Gad Avigad, Barbara Brodsky and Eric F. Eikenberry, *J. Mol. Biol.* (1988), 203, 495–505; and a manuscript entitled Isolation and Partial Characterization of Collagen Chains Dimerized by Sugar-Derived Cross-Links by Shizuko Tanaka, Gad Avigad, Eric F. Eikenberry and Barbara Brodsky to be published in *J. Biol. Chem.* (1988).

REFERENCES OF INTEREST AS BACKGROUND TO INVENTION

1. Andreassen, T. T., and Oxlund, H. (1985), *Diabetologia*, 28, 687-691.
2. Andreassen, T. T., Seyer-Hansen, K., and Bailey, A. J. (1981), *Biochem. Biophys Acta*, 677, 313-317.
3. Angyal, S. J. (1984), *Adv. Carbohydr. Chem. Biochem.*, 42, 15-68.
4. Archarya, A. S., and Sussman, L. G. (1984), *J. Biol. Chem.*, 259, 4372-4378.
5. Avigad, G. (1983), *Anal. Biochem.*, 134, 499-504.
6. Bassiouny, A. R., Rosenberg, H., and McDonald, T. L. (1983), *Diabetes*, 32, 1182-1184.
7. Bensusan, H. B. (1986), In "Structure and Function of Connective and Skeletal Tissue", Fitton-Jackson, S., Harkness, R. D., Partridge, S. M., and Tristram, G. R., Eds., *Butterworths*, London, pp. 42-46.
8. Berg, R. A. (1982), In "Methods in Enzymology", Cunningham, L. W., and Fredericksen, D. W., Eds., *Academic Press*, New York, Vol. 82 (part A), pp. 372-397.
9. Birk, D. E., and Silver, F. H. (1983), *Int. J. Biol. Macromol.*, 5, 209-214.
10. Brodsky, B., Eikenberry, E. F., Belbruno, K. C., and Sterling K. (1982), *Biopolymers*, 21, 935-951.
11. Brownlee, M., Vlassara, H., and Cerami, A. (1984), *Ann. Int. Med.*, 101, 527-537.
12. Brownlee, M., Vlassara, H., Kooney, A., Ulrich, P., and Cerami, A. (1986), *Science*, 232, 1629-1632.
13. Bunn, H. F., Gabbay, K. H., and Gallop, P. M. (1978), *Science*, 200, 21-27.
14. Bunn, H. F., and Higgins, P. J. (1981), *Science*, 213, 222-224.
15. Cerami, A., Vlassara, H., and Brownlee, M. (1985), *Metabolism*, 34, (Suppl. 1), 37-44.
16. Cerami, A., Vlassara, H., and Brownlee, M. (1986), *J. Cell. Biochem.*, 30, 111-120.
17. Chamberlain, T. P. (1979), *Anal. Biochem.*, 98, 132-135.
18. Chang, J. C. F., Ulrich, P. C., Bucala, R., and Cerami, A. (1985), *J. Biol. Chem.*, 260, 7970-7974.
19. Chapman, J. A., and Hulmes, D. J. S. (1984), In Ultrastructure of the Connective Tissue Matrix, (Ruggeri, A., and Motta, P.M., Eds.), pp. 1-33, *Martinus Nijhoff*, Boston.
20. Chew, M. W. K., and Squire, J. M. (1986), *Int. J. Biol. Macromol.*, 8, 27-36.
21. Cohen, M. P., and Yu-Wu, V. (1983), *Exp. Gerontol.*, 18, 461-469.
22. Comper, W. D., and Laurent, T. C. (1978), *Physiol. Rev.*, 58, 255-315.
23. Duncan, B. B., and Heiss, G. (1984), *Amer. J. Epidemiol.*, 120, 169-189.
24. Eble, A. S., Thorpe, S. R., and Baynes, J. W. (1983), *J. Biol. Chem.*, 258, 9406-9412.
25. Eikenberry, E. F., Childs, B., Sheren, S. B., Parry, D. A. D., Craig, A. S., and Brodsky, B. (1984), *J. Mol. Biol.*, 176, 261-277.
26. Eikenberry, E. F., Tanaka, S., Avigad, G., and Brodsky, B. (1987), *Biophys. J.*, 51, 458a.
27. Eyre, D. R., Paz, M. A., and Gallop, P. M. (1984), *Ann. Rev. Biochem.*, 53, 717-748.
28. Fraser, R. D. B., and MacRae, T. P. (1981), *Int. J. Biol. Macromol.*, 3, 193-200.
29. Fraser, R. D. B., MacRae, T. P., and Miller, A. (1987), *J. Mol. Biol.*, 193, 115-125.
30. Fraser, R. D. B., MacRae, T. P., Miller, A., and Suzuki, E. (1983), *J. Mol. Biol.*, 167, 497-521.
31. Fraser, R. D. B., MacRae, T. P., and Suzuki, E. (1979), *J. Mol. Biol.*, 129, 463-481.
32. Fujii, K., and Tanzer, M. L. (1974), *FEBS Letters*, 43, 300-302.
33. Furberg, A. (1960), *Acta Chcm. Scand.*, 14, 1357-1363.
34. Gallop, P. M., Fluckiger, R., Hanneken, A., Mininsohn, M. M., and Gabbay, KnH. (1981), *Anal. Biochem.*, 117, 427-432.
35. Grynpas, M. D., Eyre, D. R., and Kirschner, D. A. (1980), *Biochem. Biophys. Acta*, 626, 346-3535.
36. Guitton, J. D., LePape, A., and Muh, J.-P. (1984), *Collagen Rel. Res.*, 4, 253-264.
37. Hamlin, C. R., and Kohn, R. R. (1971), *Biochem. Biophys. Acta*, 236, 458-467.
38. Hamlin, C. R., Kohn, R. R., and Luschin, J. H. (1975), *Diabetes*, 24, 902-904.
39. Hoffman, H., Voss, T., Kuhn, K., and Engel, J. (1984), *J. Mol. Biol.*, 172, 325-343.
40. Hulmes, D. J. S., Miller, A., White, S. W., and Doyle, B. B. (1977), *J. Mol. Biol.*, 110, 643-666.
41. Kennedy, L., and Baynes, J. W. (1984), *Diabetologia*, 26, 93-98.
42. Kent, M. J. C., Light, N. D., and Bailey, A. J. (1985), *Biochem. J.*, 225, 745-752.
43. Kohn, R. R. (1983), *Conn. Tiss. Res.*, 11, 169-173.
44. Kohn, R. R., Cerami, A., and Monnier, V. M. (1984), *Diabetes*, 33, 57-59.
45. Laemlli, U. K. (1970), *Nature*, 227, 680-685.
46. LePape, A., Guitton, J. D., and Muh, J. P. (1984), *FEBS Lett.*, 170, 23-27.
47. LePape, A., Gutman, N., Guitton, J.-D., Legrand, Y., and Muh, J.-P. (1983), *Biochem. Biophys. Res. Commun.*, 111, 602-610.
48. LePape, A., Muh, J.-P., and Bailey, A. J. (1981), *Biochem. J.*, 197, 405-412.
49. Light, N. D., and Bailey, A. J. (1980), In Biology of Collagen (Viidik, A., and Vuust, J., Eds.), pp. 15-38, *Academic Press. London*.
50. Monnier, V. M., Kohn, R. R., and Cerami, A. (1984), *Proc. Natl. Acad. Sci.*, 81, 583-587.
51. Monnier, V. M., Vishwanath, V., Frank, K. E., Elmets, C. A., Dauchot, P., and Kohn, R. R. (1986), *New Engl. J. Med.*, 314, 403-408.
52. Nestler, F. H. M., Hvidt, S., Ferry, J. D., and Veis, A. (1983), *Biopolymers*, 22, 1747-1758.
53. Oimomi, M., Kitamura, Y., Nishimoto, S., Matsumoto, S., Hatanaka, H., and Baba, S. (1986), *J. Gerontol.*, 41, 695-698.
54. Perejda, A. J., Zaragoza, E. J., Eriksen, E., and Uitto, J. (1984), *Coll. Rel. Res.*, 4, 427-439.
55. Piez, K. A., Eigner, E. A., and Lewis, M. S. (1983), *Biochemistry*, 2, 58-66.
56. Pongor, S., Ulrich, P. C., Bencsath, A., and Cerami, A. (1984), *Proc. Natl. Acad. Sci.*, 81, 2684-2688.
57. Robins, S. P., and Bailey, A. J. (1972), *Biochem. Biophys. Res. Commun.*, 48, 76-84.
58. Rogozinski, S., Blumenfeld, O. O., and Seifter, S. (1983), *Arch. Biochem. Biophys.*, 221, 428-437.
59. Rosenberg, H., Modrak, J. B., Hassing, J. M., Al-Turk, W. A., and Stohs, S. J. (1979), *Biochem. Biophys. Res. Commun.*, 91, 498-501.
60. Schleicher, E., and Wieland, O.H. (1986), *Biochem. Biophys. Acta*, 884, 199-205.
61. Schnider, S. L., and Kohn, R. R. (1980a), *J. Clin. Invest.*, 66, 1179-1181.

62. S. L., and Kohn, R. R. (1980b), *J. Clin. Invest.*, 67, 1630–1635.
63. Schnider, S. L., and Kohn, R. R. (1981), *J. Clin. Invest.*, 67, 1630–1635.
64. Studier, F. W. (1973), *J. Mol. Biol.*, 79, 237–248.
65. Tanaka, S., Kelly, J., Eikenberry, E. F., Brodsky, B., and Avigad, G. (1986), 191st Meeting, American Chemical Society, New York City, *Abst. Carb.*, 35.
66. Trueb, B., Fluckiger, R., and Winterhalter, K. H. (1984), *Collagen Rel. Res.*, 4, 239–251.
67. Trueb, B., Holenstein, C. G., Fischer, R. W., and Winterhalter, K. H. (1980), *J. Biol. Chem.*, 255, 6717–6720.
68. Vishwanath, V., Frank, K. E., Elmets, C. A., Dauchot, P. J., and Monnier, V. M. (1986), *Diabetes*, 35, 916–921.
69. Vlasara, H., Brownlee, M., and Cerami, A. (1986), *Clin. Chem*, 32, B37–B41.
70. Vogt, B. W., Schleicher, E. D., and Wieland, O. H. (1982), *Diabetes*, 31, 1123–1127.
71. Yamauchi, M., Katz, E. P., and Mechanic, G. L. (1980), *Biochemistry*, 25, 4907–4913.
72. Yosha, S. F., Elden, H. R., Rabinovitch, A., Mintz, D. H., and Boucek, R. J. (1983), *Diabetes*, 32, 739–742.
73. Yue, D. K., McLennan, S., Delbridge, L., Handelsman, D. J., Reeve, T., and Turtle, J. R. (1983), *Diabetologia*, 24, 282–285.

We claim:

1. A biodegradable collagen matrix cross-linked with D-ribose.
2. The matrix of claim 1, wherein the matrix modulus is at least about 2 mPa.
3. The matrix of claim 1, wherein the modulus is at least about 4 mPa.
4. The matrix of claim 2, wherein the D-ribose condenses with collagen at a rate ($k_1$) of at least about $9.0 \times 10^{-3}$ mM/hour in an incubation solution consisting of distilled water and reactive sugar at 37° C.
5. The matrix of claim 1, wherein the matrix is substantially non-toxic and non-antigenic.
6. The matrix of claim 1, which contains at least about 0.1 mol D-ribose residues per mol of α-chain collagen.
7. The matrix of claim 1, in the form of a sheet, tube, or sponge.
8. A surgical implant comprising of the matrix of claim 1.
9. A wound dressing comprising the matrix of claim 1.
10. The dressing of claim 9, wherein the wound is a skin wound.
11. A process for preparing a biodegradable D-ribose cross-linked collagen matrix which comprises cross-linking purified collagen with D-ribose.
12. The process of claim 11, wherein the matrix is cross-linked to provide a matrix modulus of at least about 2 mPa.
13. The process of claim 12, wherein the matrix is cross-linked to provide a matrix modulus of at least about 4 mPa.
14. The process of claim 11, wherein the matrix is formed into a sheet, tube, or sponge.
15. The process of claim 12, wherein the matrix modulus is attained in no more than about two weeks.
16. The process of claim 15, wherein the matrix modulus is attained in no more than about one week.
17. The process of claim 11, wherein the collagen is incubated with an aqueous solution of D-ribose at a concentration of from about 0.1 to 0.5 M.
18. A process for promoting the healing of a wound which comprises dressing the wound with the cross-linked collagen matrix of claim 1, and thereby promoting the ingrowth of fibroblasts.
19. The process of claim 1, wherein the wound is a skin wound.
20. The biodegradable collagen matrix of claim 1, wherein the mol ratio of cross-linked ribose-residue to a α-chain collagen content does not exceed a ratio of about 1 to 1, thereby minimizing destabilization of the matrix.
21. A wound dressing or surgical implant which comprises the biodegradable collagen matrix of claim 20.

* * * * *

UNITED STATES PATENT AND TRADEMARK OFFICE
CERTIFICATE OF CORRECTION

PATENT NO. : 4,971,954
DATED : November 20, 1990
INVENTOR(S) : Brodsky, Barbara et al.

It is certified that error appears in the above-identified patent and that said Letters Patent is hereby corrected as shown below:

Column 1,
Line 5, before "BACKGROUND OF THE INVENTION," insert the following paragraph:
-- STATEMENT REGARDING FEDERALLY SPONSORED RESEARCH OR DEVELOPMENT:
    This invention was made with government support under Grant No. AR19626 awarded by National Institutes of Health. The Government has certain rights in the invention. --

Signed and Sealed this

Eighth Day of July, 2003

JAMES E. ROGAN
*Director of the United States Patent and Trademark Office*